(12) United States Patent
el Kaliouby et al.

(10) Patent No.: US 9,503,786 B2
(45) Date of Patent: *Nov. 22, 2016

(54) VIDEO RECOMMENDATION USING AFFECT

(71) Applicant: Affectiva, Inc., Waltham, MA (US)

(72) Inventors: Rana el Kaliouby, Milton, MA (US); Abdelrahman Mahmoud, Somerville, MA (US); Panu James Turcot, San Francisco, CA (US)

(73) Assignee: Affectiva, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,896

(22) Filed: Aug. 10, 2015

(65) Prior Publication Data

US 2015/0350730 A1 Dec. 3, 2015

Related U.S. Application Data

(63) Continuation-in-part of application No. 13/406,068, filed on Feb. 27, 2012, now Pat. No. 9,106,958, and a continuation-in-part of application No. 14/796,419, filed on Jul. 10, 2015, which is a continuation-in-part (Continued)

(51) Int. Cl.
*H04H 60/33* (2008.01)
*H04N 21/466* (2011.01)

(Continued)

(52) U.S. Cl.
CPC ........... *H04N 21/4668* (2013.01); *A61B 5/165* (2013.01); *G06Q 30/0631* (2013.01); *H04N 21/251* (2013.01); *H04N 21/4223* (2013.01); *H04N 21/44218* (2013.01); *H04N 21/4667* (2013.01); *G06K 2009/00328* (2013.01)

(58) Field of Classification Search
None
See application file for complete search history.

(56) References Cited

U.S. PATENT DOCUMENTS 3,034,500 A 5/1962 Backster, Jr.
3,548,806 A 12/1970 Fisher (Continued)

FOREIGN PATENT DOCUMENTS

JP 08115367 7/1996
KR 10-2005-0021759 A 3/2005

(Continued)

OTHER PUBLICATIONS

Rana Ayman El Kaliouby, Mind-reading machines: automated inference of complex mental states, Jul. 2005, University of Cambridge, Cambridge, United Kingdom.

(Continued)

*Primary Examiner* — John Schnurr
*Assistant Examiner* — Cynthia Fogg
(74) *Attorney, Agent, or Firm* — Adams Intellex, PLC

(57) ABSTRACT

Analysis of mental states is provided to enable data analysis pertaining to video recommendation based on affect. Analysis and recommendation can be for socially shared livestream video. Video response may be evaluated based on viewing and sampling various videos. Data is captured for viewers of a video where the data includes facial information and/or physiological data. Facial and physiological information may be gathered for a group of viewers. In some embodiments, demographics information is collected and used as a criterion for visualization of affect responses to videos. In some embodiments, data captured from an individual viewer or group of viewers is used to rank videos.

18 Claims, 15 Drawing Sheets

Related U.S. Application Data of application No. 13/153,745, filed on Jun. 6, 2011, said application No. 14/796,419 is a continuation-in-part of application No. 14/460,915, filed on Aug. 15, 2014, which is a continuation-in-part of application No. 13/153,745, filed on Jun. 6, 2011.

(60) Provisional application No. 61/447,089, filed on Feb. 27, 2011, provisional application No. 61/447,464, filed on Feb. 28, 2011, provisional application No. 61/467,209, filed on Mar. 24, 2011, provisional application No. 61/549,560, filed on Oct. 20, 2011, provisional application No. 61/568,130, filed on Dec. 7, 2011, provisional application No. 61/580,880, filed on Dec. 28, 2011, provisional application No. 61/581,913, filed on Dec. 30, 2011, provisional application No. 61/023,800, filed on Jul. 11, 2014, provisional application No. 62/047,508, filed on Sep. 8, 2014, provisional application No. 62/082,579, filed on Nov. 20, 2014, provisional application No. 62/128,974, filed on Mar. 5, 2015, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/867,007, filed on Aug. 16, 2013, provisional application No. 61/924,252, filed on Jan. 7, 2014, provisional application No. 61/916,190, filed on Dec. 14, 2013, provisional application No. 61/927,481, filed on Jan. 15, 2014, provisional application No. 61/953,878, filed on Mar. 16, 2014, provisional application No. 61/972,314, filed on Mar. 30, 2014, provisional application No. 62/023,800, filed on Jul. 11, 2014, provisional application No. 61/352,166, filed on Jun. 7, 2010.

(51) Int. Cl.

| | | |
|---|---|---|
| *H04N 21/442* | (2011.01) | |
| *A61B 5/16* | (2006.01) | |
| *G06Q 30/06* | (2012.01) | |
| *H04N 21/25* | (2011.01) | |
| *H04N 21/4223* | (2011.01) | |
| *G06K 9/00* | (2006.01) | |

(56) References Cited

U.S. PATENT DOCUMENTS

| | | | |
|---|---|---|---|
| 3,870,034 A | 3/1975 | James | |
| 4,353,375 A | 10/1982 | Colburn et al. | |
| 4,448,203 A | 5/1984 | Williamson et al. | |
| 4,794,533 A | 12/1988 | Cohen | |
| 4,807,642 A | 2/1989 | Brown | |
| 4,817,628 A | 4/1989 | Zealear et al. | |
| 4,950,069 A | 8/1990 | Hutchinson | |
| 4,964,411 A | 10/1990 | Johnson et al. | |
| 5,016,282 A | 5/1991 | Tomono et al. | |
| 5,031,228 A | 7/1991 | Lu | |
| 5,219,322 A | 6/1993 | Weathers | |
| 5,247,938 A | 9/1993 | Silverstein et al. | |
| 5,259,390 A | 11/1993 | Maclean | |
| 5,507,291 A | 4/1996 | Stirbl et al. | |
| 5,572,596 A | 11/1996 | Wildes et al. | |
| 5,619,571 A | 4/1997 | Sandstrom et al. | |
| 5,647,834 A | 7/1997 | Ron | |
| 5,649,061 A | 7/1997 | Smyth | |
| 5,663,900 A | 9/1997 | Bhandari et al. | |
| 5,666,215 A | 9/1997 | Fredlund et al. | |
| 5,725,472 A | 3/1998 | Weathers | |
| 5,741,217 A | 4/1998 | Gero | |
| 5,760,917 A | 6/1998 | Sheridan | |
| 5,762,611 A | 6/1998 | Lewis et al. | |
| 5,772,591 A | 6/1998 | Cram | |
| 5,774,591 A | 6/1998 | Black et al. | |
| 5,802,220 A | 9/1998 | Black et al. | |
| 5,825,355 A | 10/1998 | Palmer et al. | |
| 5,886,683 A | 3/1999 | Tognazzini et al. | |
| 5,898,423 A | 4/1999 | Tognazzini et al. | |
| 5,920,477 A | 7/1999 | Hoffberg et al. | |
| 5,945,988 A | 8/1999 | Williams et al. | |
| 5,959,621 A | 9/1999 | Nawaz et al. | |
| 5,969,755 A | 10/1999 | Courtney | |
| 5,983,129 A | 11/1999 | Cowan et al. | |
| 5,987,415 A | 11/1999 | Breese et al. | |
| 6,004,061 A | 12/1999 | Manico et al. | |
| 6,004,312 A | 12/1999 | Finneran et al. | |
| 6,008,817 A | 12/1999 | Gilmore, Jr. | |
| 6,026,321 A | 2/2000 | Miyata et al. | |
| 6,026,322 A | 2/2000 | Korenman et al. | |
| 6,056,781 A | 5/2000 | Wassick et al. | |
| 6,067,565 A | 5/2000 | Horvitz | |
| 6,088,040 A | 7/2000 | Oda et al. | |
| 6,099,319 A | 8/2000 | Zaltman et al. | |
| 6,134,644 A | 10/2000 | Mayuzumi et al. | |
| 6,182,098 B1 | 1/2001 | Selker | |
| 6,185,534 B1 | 2/2001 | Breese et al. | |
| 6,195,651 B1 | 2/2001 | Handel et al. | |
| 6,212,502 B1 | 4/2001 | Ball et al. | |
| 6,222,607 B1 | 4/2001 | Szajewski et al. | |
| 6,309,342 B1 | 10/2001 | Blazey et al. | |
| 6,327,580 B1 | 12/2001 | Pierce et al. | |
| 6,349,290 B1 | 2/2002 | Horowitz et al. | |
| 6,351,273 B1 | 2/2002 | Lemelson et al. | |
| 6,437,758 B1 | 8/2002 | Nielsen et al. | |
| 6,443,840 B2 | 9/2002 | Von Kohorn | |
| 6,530,082 B1 | 3/2003 | Del Sesto et al. | |
| 6,577,329 B1 | 6/2003 | Flickner et al. | |
| 6,606,102 B1 | 8/2003 | Odom | |
| 6,629,104 B1 | 9/2003 | Parulski et al. | |
| 6,792,458 B1 | 9/2004 | Muret et al. | |
| 6,847,376 B2 | 1/2005 | Engeldrum et al. | |
| 7,013,478 B1* | 3/2006 | Hendricks | G06F 17/30017 348/E5.002 |
| 7,113,916 B1 | 9/2006 | Hill | |
| 7,120,880 B1 | 10/2006 | Dryer et al. | |
| 7,197,459 B1 | 3/2007 | Harinarayan et al. | |
| 7,233,684 B2 | 6/2007 | Fedorovskaya et al. | |
| 7,246,081 B2 | 7/2007 | Hill | |
| 7,263,474 B2 | 8/2007 | Fables et al. | |
| 7,266,582 B2 | 9/2007 | Stelting | |
| 7,307,636 B2 | 12/2007 | Matraszek et al. | |
| 7,327,505 B2 | 2/2008 | Fedorovskaya et al. | |
| 7,350,138 B1 | 3/2008 | Swaminathan et al. | |
| 7,353,399 B2 | 4/2008 | Ooi et al. | |
| 7,355,627 B2 | 4/2008 | Yamazaki et al. | |
| 7,428,318 B1 | 9/2008 | Madsen et al. | |
| 7,474,801 B2 | 1/2009 | Teo et al. | |
| 7,496,622 B2 | 2/2009 | Brown et al. | |
| 7,549,161 B2 | 6/2009 | Poo et al. | |
| 7,551,755 B1 | 6/2009 | Steinberg et al. | |
| 7,555,148 B1 | 6/2009 | Steinberg et al. | |
| 7,558,408 B1 | 7/2009 | Steinberg et al. | |
| 7,564,994 B1 | 7/2009 | Steinberg et al. | |
| 7,573,439 B2 | 8/2009 | Lau et al. | |
| 7,580,512 B2 | 8/2009 | Batni et al. | |
| 7,584,435 B2 | 9/2009 | Bailey et al. | |
| 7,587,068 B1 | 9/2009 | Steinberg et al. | |
| 7,610,289 B2 | 10/2009 | Muret et al. | |
| 7,620,934 B2 | 11/2009 | Falter et al. | |
| 7,644,375 B1 | 1/2010 | Anderson et al. | |
| 7,676,574 B2 | 3/2010 | Glommen et al. | |
| 7,826,657 B2 | 11/2010 | Zhang et al. | |
| 7,830,570 B2 | 11/2010 | Morita et al. | |
| 7,881,493 B1 | 2/2011 | Edwards et al. | |
| 7,921,036 B1 | 4/2011 | Sharma | |
| 8,010,458 B2 | 8/2011 | Galbreath et al. | |
| 8,401,248 B1 | 3/2013 | Moon et al. | |
| 8,442,638 B2 | 5/2013 | Libbus et al. | |

(56) References Cited

U.S. PATENT DOCUMENTS

| | | | |
|---|---|---|---|
| 8,522,779 B2 | 9/2013 | Lee et al. | |
| 8,600,120 B2 | 12/2013 | Gonion et al. | |
| 2001/0033286 A1 | 10/2001 | Stokes et al. | |
| 2001/0041021 A1 | 11/2001 | Boyle et al. | |
| 2002/0007249 A1 | 1/2002 | Cranley | |
| 2002/0030665 A1 | 3/2002 | Ano | |
| 2002/0042557 A1 | 4/2002 | Bensen et al. | |
| 2002/0054174 A1 | 5/2002 | Abbott et al. | |
| 2002/0084902 A1 | 7/2002 | Zadrozny et al. | |
| 2002/0171551 A1 | 11/2002 | Eshelman et al. | |
| 2002/0182574 A1 | 12/2002 | Freer | |
| 2003/0035567 A1 | 2/2003 | Chang et al. | |
| 2003/0037041 A1 | 2/2003 | Hertz | |
| 2003/0060728 A1 | 3/2003 | Mandigo | |
| 2003/0093784 A1* | 5/2003 | Dimitrova | H04N 7/163 725/10 |
| 2003/0191682 A1 | 10/2003 | Shepard et al. | |
| 2003/0191816 A1 | 10/2003 | Landress et al. | |
| 2004/0181457 A1 | 9/2004 | Biebesheimer | |
| 2005/0187437 A1 | 8/2005 | Matsugu | |
| 2005/0283055 A1 | 12/2005 | Shirai et al. | |
| 2005/0289582 A1 | 12/2005 | Tavares et al. | |
| 2006/0019224 A1 | 1/2006 | Behar et al. | |
| 2006/0143647 A1 | 6/2006 | Bill | |
| 2006/0235753 A1 | 10/2006 | Kameyama | |
| 2007/0167689 A1 | 7/2007 | Ramadas et al. | |
| 2007/0239787 A1 | 10/2007 | Cunningham et al. | |
| 2007/0255831 A1 | 11/2007 | Hayashi et al. | |
| 2007/0299964 A1 | 12/2007 | Wong et al. | |
| 2008/0091512 A1 | 4/2008 | Marci et al. | |
| 2008/0091515 A1 | 4/2008 | Thieberger et al. | |
| 2008/0101660 A1 | 5/2008 | Seo | |
| 2008/0103784 A1 | 5/2008 | Wong et al. | |
| 2008/0184170 A1 | 7/2008 | Periyalwar | |
| 2008/0208015 A1 | 8/2008 | Morris et al. | |
| 2008/0221472 A1 | 9/2008 | Lee et al. | |
| 2008/0222670 A1* | 9/2008 | Lee | G09B 7/02 725/10 |
| 2008/0287821 A1 | 11/2008 | Jung et al. | |
| 2009/0006206 A1 | 1/2009 | Groe | |
| 2009/0083421 A1 | 3/2009 | Glommen et al. | |
| 2009/0094286 A1 | 4/2009 | Lee et al. | |
| 2009/0112694 A1 | 4/2009 | Jung et al. | |
| 2009/0112810 A1 | 4/2009 | Jung et al. | |
| 2009/0133048 A1 | 5/2009 | Gibbs et al. | |
| 2009/0150919 A1* | 6/2009 | Lee | H04N 7/17309 725/10 |
| 2009/0210290 A1 | 8/2009 | Elliott et al. | |
| 2009/0217315 A1 | 8/2009 | Malik et al. | |
| 2009/0259518 A1 | 10/2009 | Harvey | |
| 2009/0270170 A1 | 10/2009 | Patton | |
| 2009/0271417 A1 | 10/2009 | Toebes et al. | |
| 2009/0299840 A1 | 12/2009 | Smith | |
| 2010/0070523 A1 | 3/2010 | Delgo et al. | |
| 2010/0099955 A1 | 4/2010 | Thomas et al. | |
| 2010/0266213 A1 | 10/2010 | Hill | |
| 2010/0274847 A1 | 10/2010 | Anderson et al. | |
| 2010/0324437 A1 | 12/2010 | Freeman | |
| 2011/0126226 A1 | 5/2011 | Makhlouf | |
| 2011/0143728 A1 | 6/2011 | Holopainen et al. | |
| 2011/0196855 A1 | 8/2011 | Wable et al. | |
| 2011/0231240 A1 | 9/2011 | Schoen et al. | |
| 2011/0251493 A1 | 10/2011 | Poh et al. | |
| 2011/0263946 A1 | 10/2011 | el Kaliouby et al. | |
| 2012/0124456 A1* | 5/2012 | Perez | G06Q 30/02 715/200 |
| 2012/0324491 A1* | 12/2012 | Bathiche | H04H 60/33 725/10 |
| 2013/0116587 A1 | 5/2013 | Sornmo et al. | |
| 2013/0197409 A1 | 8/2013 | Baxter et al. | |
| 2013/0242064 A1* | 9/2013 | Herdy | H04N 5/4403 348/51 |
| 2015/0135225 A1* | 5/2015 | Bayer | H04N 21/4826 725/46 |

FOREIGN PATENT DOCUMENTS

| | | | |
|---|---|---|---|
| KR | 10-2008-0016303 A | 2/2008 | |
| KR | 1020100048688 A | 5/2010 | |
| WO | WO 2011/045422 A1 | 4/2011 | |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

* cited by examiner

VIDEO RECOMMENDATION USING AFFECT

RELATED APPLICATIONS

This application is a continuation-in-part of U.S. patent application "Video Recommendation Based on Affect" Ser. No. 13/406,068, filed Feb. 27, 2012, which claims the benefit of U.S. provisional patent applications "Recommendation and Visualization of Affect Responses to Videos" Ser. No. 61/447,089, filed Feb. 27, 2011, "Video Ranking Based on Affect" Ser. No. 61/447,464, filed Feb. 28, 2011, "Baseline Face Analysis" Ser. No. 61/467,209, filed Mar. 24, 2011, "Mental State Analysis of Voters" Ser. No. 61/549,560, filed Oct. 20, 2011, "Mental State Evaluation Learning for Advertising" Ser. No. 61/568,130, filed Dec. 7, 2011, "Affect Based Concept Testing" Ser. No. 61/580,880, filed Dec. 28, 2011, and "Affect Based Evaluation of Advertisement Effectiveness" Ser. No. 61/581,913, filed Dec. 30, 2011. This application is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015; "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011; and "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014; and "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. Each of the foregoing applications is hereby incorporated by reference in its entirety.

FIELD OF INVENTION

This application relates generally to analysis of mental states and more particularly to making video recommendations based on affect.

BACKGROUND

People spend a tremendous amount of time engaged in viewing and interacting with videos. The videos may be watched in numerous contexts including education, entertainment, obtaining daily news, watching the latest movies, and many others. A video may be a movie, a television show, a web series, a webisode, a video, a music video, or a video clip. The video may be viewed as a stand-alone element on an electronic display, or may be part of a webpage. Evaluation of these videos and people's responses to them is exceedingly important to gauging the effectiveness of education, commerce, and entertainment. People can self-rate videos in a tedious fashion of entering a specific number of stars corresponding to a level of like or dislike, or may even answer a list of questions. It is even more tedious and difficult to evaluate portions of videos, where evaluation of a brief period of time from a video may be useful. Recommendations based on such a star rating are imprecise, subjective, and often unreliable.

SUMMARY

A computer implemented method is disclosed for affect based recommendations comprising: playing a first media presentation to an individual; capturing mental state data for the individual while the first media presentation is played; and recommending a second media presentation to the individual based on the mental state data for the individual which was captured. The method may further comprise analyzing the mental state data to produce mental state information. The method may further comprise correlating the mental state data which was captured for the individual to mental state data collected from other people who experienced the first media presentation. The recommending the second media presentation to the individual may be further based on the correlating between the individual and the other people. The first media presentation may include one of a group consisting of a movie, a television show, a web series, a webisode, a video, a video clip, an electronic game, an e-book, and an e-magazine. The second media presentation may include one of a group consisting of a movie, a television show, a web series, a webisode, a video, a video clip, an electronic game, an e-book, and an e-magazine. The first media presentation may be played on a web-enabled interface. The first media presentation may include one of a YouTube™, a Vimeo™ video, and a Netflix™ video. The second media presentation may include one of a YouTube™, a Vimeo™ video, and a Netflix™ video. The method may further comprise ranking the first media presentation relative to another media presentation based on the mental state data which was captured. The ranking may be for the individual based on the mental state data from the individual. The ranking may be based on anticipated preferences for the individual.

The mental state data may be captured from multiple people and further comprising aggregating the mental state data from the multiple people. The method may further comprise ranking the first media presentation relative to another media presentation based on the mental state data which was aggregated from the multiple people. The mental state data may include one of a group consisting of physiological data, facial data, and actigraphy data. The facial data may include information on one or more of a group consisting of facial expressions, action units, head gestures, smiles, brow furrows, squints, lowered eyebrows, raised eyebrows, smirks, and attention. The physiological data may include one or more of electrodermal activity, heart rate, heart rate variability, skin temperature, and respiration. The method may further comprise inferring of mental states based on the mental state data which was collected. The mental states may include one of a group consisting of frustration, confusion, disappointment, hesitation, cognitive overload, focusing, being engaged, attending, boredom, exploration, confidence, trust, delight, valence, skepticism, and satisfaction. The playing of the first media presentation may be done on a mobile device and further comprising recording of facial images with the mobile device as part of the capturing of the mental state data.

In embodiments, a computer program product embodied in a non-transitory computer readable medium may comprise: code for playing a first media presentation to an individual; code for capturing mental state data for the individual while the first media presentation is played; and code for recommending a second media presentation to the individual based on the mental state data for the individual which was captured. In some embodiments, a computer system for affect based recommendations may comprise: a memory for storing instructions; one or more processors attached to the memory wherein the one or more processors are configured to: play a first media presentation to an individual; capture mental state data for the individual while the first media presentation is played; and recommend a second media presentation to the individual based on the mental state data for the individual which was captured.

In some embodiments, a computer implemented method for affect based ranking may comprise: displaying a plurality of media presentations to a group of people; capturing mental state data from the group of people while the plurality of media presentations is displayed; correlating the mental state data captured from the group of people who viewed the plurality of media presentations; and ranking the media presentations relative to one another based on the mental state data. The method may further comprise tagging the plurality of media presentations with mental state information based on the mental state data which was captured.

Various features, aspects, and advantages of numerous embodiments will become more apparent from the following description.

BRIEF DESCRIPTION OF THE DRAWINGS

The following detailed description of certain embodiments may be understood by reference to the following figures wherein.

DETAILED DESCRIPTION

The present disclosure provides a description of various methods and systems for analyzing people's mental states as they view videos. The ability to properly evaluate people's response to videos enables accurate recommendation of other videos. These videos can be for any purpose, including, but not limited to, entertainment, education, or general information. Evaluation of mental states in response to videos provides unmatched insight into people's true reactions to these videos. A mental state may be an emotional state or a cognitive state. Examples of emotional states include happiness or sadness. Examples of cognitive states include concentration or confusion. Observing, capturing, and analyzing these mental states can yield significant information about people's reactions to a videos. Some terms commonly used in evaluation of mental states are arousal and/or valence. Arousal is an indication on the amount of activation or excitement of a person. Valence is an indication on whether a person is positively or negatively disposed. Affect may include analysis of arousal and valence. Affect may also include facial analysis for expressions such as smiles or brow furrowing. Analysis may be as simple as tracking when someone smiles or when someone frowns while viewing a video. Recommendations for other videos may, in some embodiments, be made based on tracking when someone smiles while watching one or more videos and recommending videos with similarities to those which made the individual smile.

Figure 1:
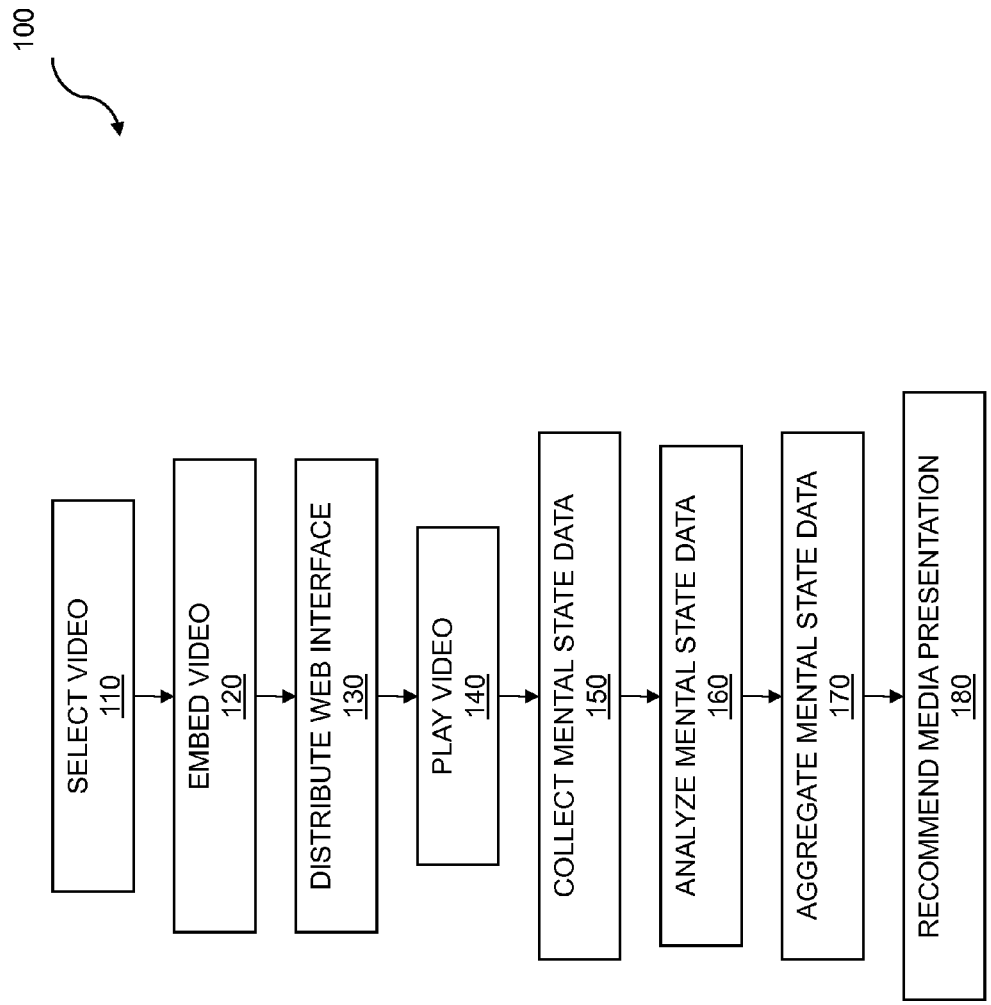
FIG. 1 is a flow diagram for displaying a video.

FIG. 1 is a flow diagram for displaying a video. A flow 100 is given for a computer-implemented method for rendering video. The flow 100 may begin with selecting a video 110. The video may be selected by a system which is automating the collection of affect on numerous videos. In embodiments, the video may be selected by a person who wants affect collected on the video. The video may include one of a YouTube™ and a Vimeo™ video. The flow 100 may continue with embedding the video 120 within a web-enabled interface wherein the web-enabled interface activates collecting of mental state data. The web-enabled interface may include a web page, web application, or the like. The embedding 120 may include inserting a link for the video into a URL on a web page that activates affect collection. The embedding 120 may include providing a link where a user can insert their own video. The affect may be collected by evaluating facial expressions. The evaluating facial expressions may include evaluating smiles or brow furrows. The affect may include evaluation of one of a group consisting of attention, engagement, interest, liking, and disliking. The affect may be collected by evaluating physiology.

The flow 100 continues with distributing the web-enabled interface 130. The distributing of the web-enabled interface may include sending a URL. The sending of the URL may be accomplished using one of a group consisting of an email, a text message, a Facebook™ posting, a Twitter™ message, a Google+™ posting, a LinkedIn™ posting, a social network update, and a blog entry. In some embodiments, the sending may be accomplished by pressing or selecting a button on a web page associated with a video. Selecting the button may distribute the video. In some embodiments, selecting the button may also distribute mental state data or analysis of mental state data along with the video. The flow 100 may further comprise playing of the video 140, perhaps in the web-enabled interface, and collecting the mental state data 150 while the video is being played. The mental state data may be collected for a group of people who view the video.

The mental state data collected may include one of a group consisting of physiological data, facial data, and actigraphy data. The physiological data may include one or more of electrodermal activity, heart rate, heart rate variability, skin temperature, and respiration. The facial data may include information on one or more of a group consisting of facial expressions, action units, head gestures, smiles, brow furrows, squints, lowered eyebrows, attention, and the like. The mental states that may be inferred may include one of a group consisting of frustration, confusion, disappointment, hesitation, cognitive overload, focusing, being engaged, attending, boredom, exploration, confidence, trust, delight, frustration, valence, skepticism, and so on. The mental state data may be collected for an individual. Likewise, the mental state data may be captured from multiple people.

The flow 100 may continue with analyzing mental state data 160. The mental state data may be analyzed 160 to produce mental state information. Mental states for a viewer or a plurality of viewers may be inferred based on the mental state data which was collected.

The flow 100 may continue with aggregating mental state data 170. Mental state data may be collected from multiple people who view a video, and the mental state data from the multiple people may be aggregated. Thus, the mental state data is aggregated across a group of people. Results from the aggregating 170 may be presented as part of the displaying of a graphical representation.

The flow 100 may further comprise recommending a media presentation 180. The aggregating of the mental state data 170 may be used as part of the input to result in recommending a media presentation 180 to an individual based on the mental state data which was aggregated. The media presentation may be one of a group consisting of a movie, a television show, a web series, a webisode, a video, a video clip, an electronic game, an advertisement, an e-book, and an e-magazine. The flow 100 may further comprise recommending a media presentation to a second person based on the mental state data collected from a first person. Various steps in the flow 100 may be changed in order, repeated, omitted, or the like without departing from the disclosed inventive concepts. Various embodiments of the flow 100 may be included in a computer program product embodied in a non-transitory computer readable medium that includes code executable by one or more processors. The flow 100 may include tagging the plurality of media presentations with mental state information based on the mental state data which was captured.

Figure 2:
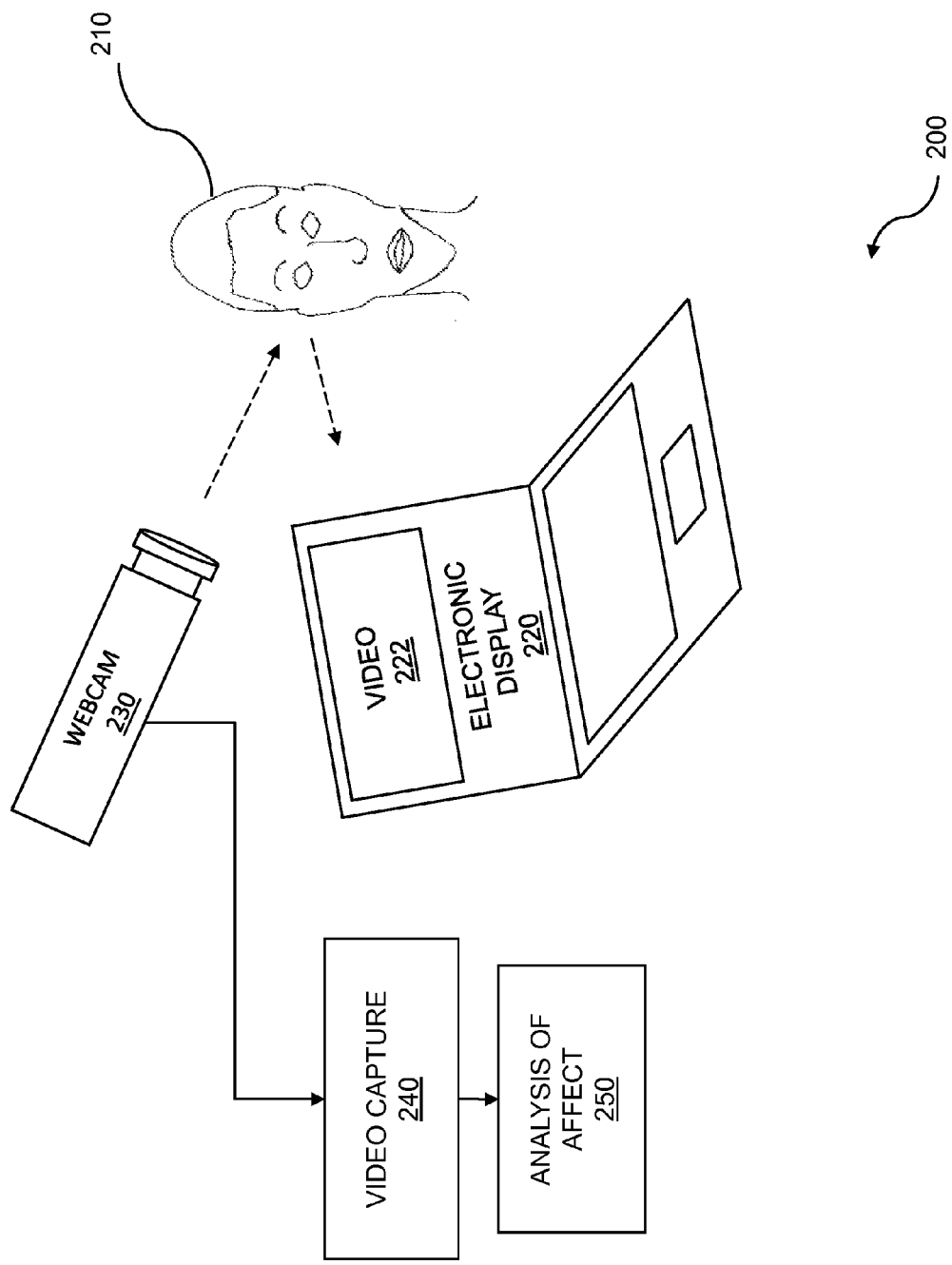
FIG. 2 is a system for capturing facial response to a video.

FIG. 2 is a system for capturing facial response to a video. A system 200 includes an electronic display 220 and a webcam 230. The system 200 captures facial response to a video 222 shown on the electronic display 220. The facial data may include video and collection of information relating to mental states. The facial data may include information on one or more of a group consisting of facial expressions, action units, head gestures, smile, brow furrows, squints, lowered eyebrows, raised eyebrows, smirks, and attention. In some embodiments, a webcam 230 may capture video of the person 210. Images of the person 210 may also be captured by a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that may allow image data captured to be used by an electronic system. The capture of the facial response of person 210 to video 222 shown on display 220 may include collection of mental state data. The capture of the facial response of person 210 to video 222 shown on display 220 may include capture of physiological data. The physiological data may include one or more of heart rate, heart rate variability, skin temperature, respiration, and the like.

The electronic display 220 may show a video. The video 222 may be shown on any electronic display, including but not limited to, a computer display, a laptop screen, a net-book screen, a tablet computer screen, a cell phone display, a mobile device display, a remote with a display, a television, a projector, or the like. The electronic display 220 may include connections to a keyboard, mouse, joystick, touchpad, wand, motion sensor, and other input means. The video 222 may be displayed within a webpage, a website, a web-enabled application, or the like. The images of the person 210 may be captured by a video capture unit 240. In some embodiments, video of the person 210 is captured while in others a series of still images are captured.

Analysis of action units, gestures, mental states, and physiological data may be accomplished using the captured images of the person 210. The action units may be used to identify smiles, frowns, and other facial indicators of mental states. The gestures, including head gestures, may indicate interest or curiosity. For example, a head gesture of moving toward the video 222 may indicate increased interest or a desire for clarification. Based on the captured images, analysis of physiology may be performed. Analysis of affect 250 may be performed based on the information and images which are captured. The analysis can include facial analysis and analysis of head gestures. The analysis can include evaluating physiology and may include evaluating one of a group consisting of heart rate, heart rate variability, respiration, perspiration, temperature, and other bodily evaluation.

Figure 3:
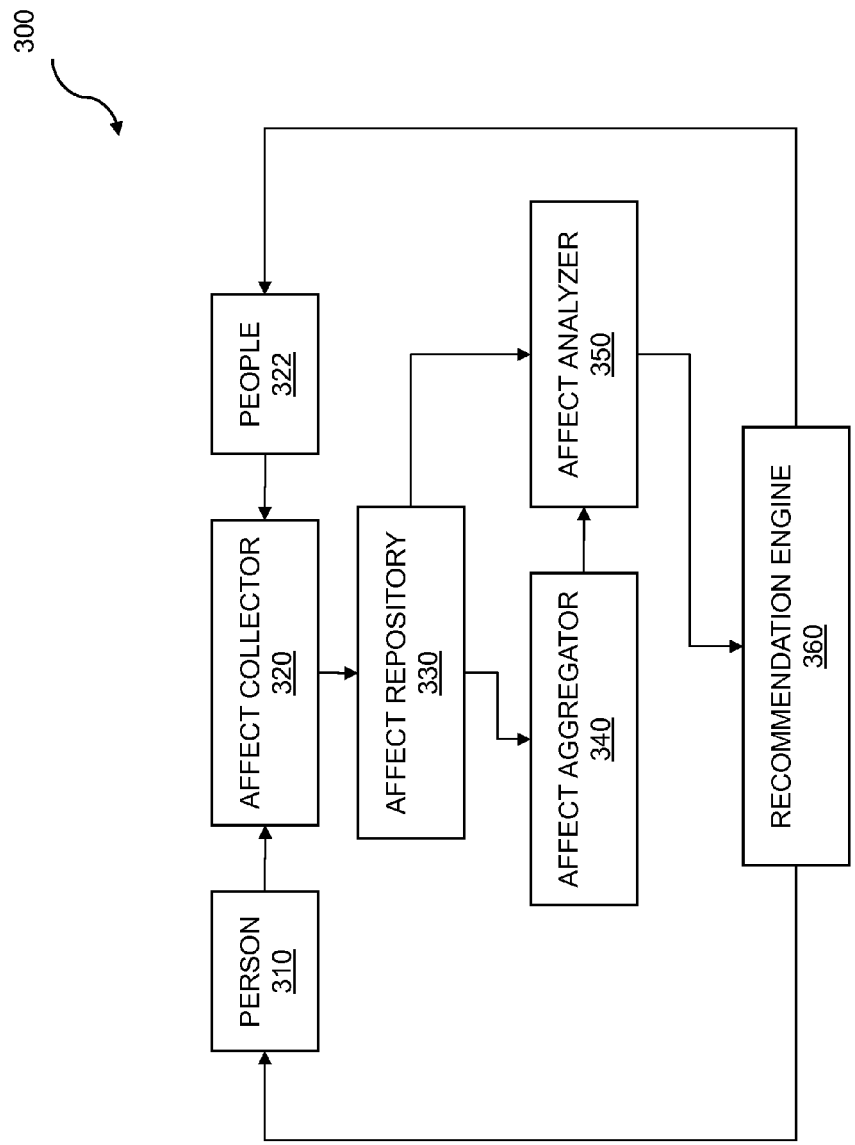
FIG. 3 is a diagram of a recommendation system.

FIG. 3 is a diagram of a recommendation system. A person 310 may view a video. While the person 310 is viewing a video, an affect collector 320 may gather affect data on the person 310. The affect collector 320 may be a webcam or other camera device. The affect collector 320 may be a biosensor attached to the person 310 in one or more locations. The affect data collected from the person 310 by the affect collector 320 can be stored in an affect repository 330. The affect repository 330 may be on a local computer or on a remote server, or may be distributed or part of a cloud computing system.

An affect analyzer 350 may analyze the affect data collected from the person 310. The affect analyzer 350 may recognize mental states including information on concentration, liking, disliking, etc. The affect analyzer 350 may recognize smiles or frowns. Based on the analysis done by the affect analyzer 350 a recommendation engine 360 may recommend a video or other media presentation to the person 310. The recommending of a media presentation to an individual may be based on the mental state data which was aggregated. The aggregated data may be for multiple videos by an individual or may be for a plurality of people. The recommendation may be based on common factors with one or more videos which the person 310 watched. For example, if the person 310 smiled for each of the videos that he or she watched with a specific actress as the main character, then the recommendation engine 360 may recommend another video with the same actress to the person 310. In another example, if a series of sports videos is liked by the person 310 then another sports video may be recommended.

Other people 322 may view the same video as the person 310. In some embodiments, multiple videos are viewed by the person 310 and the other people 322. In embodiments, different subsets of the multiple videos are viewed by each person. The affect collector 320 may capture affect data for each of the people 322. The affect collector 320 may be a single unit such as a kiosk in a mall or a device which collects affect for multiple people viewing a video in such a location as a conference room or a movie theater. Alternatively the affect collector 320 may be separate devices such as in the case where each person has their own computer, laptop, cell phone, mobile device, or the like. The affect repository 330 may retain affect data from the people on whom affect data is collected.

An affect aggregator 340 may take affect data from the affect repository and correlate affect data from the person 310 with the other people 322. The affect aggregator 340 may recognize trends for the person 310 who has watched multiple videos, or, for example, movies. The affect aggregator 340 may determine correlation vectors for the person 310 and the people 322 or a subset thereof. A correlation may be made using weighted Euclidean or Mahalanobis distance evaluation between two vectors, where a vector includes an individual's affect data. There are many ways to compute distances or similarity/dissimilarity measures. Collaborative filtering or the like may be used to aid in matching affect data between or among people. In some embodiments, a comparison is made based on the same content viewed by the person 310 and by individuals from the other people 322. When one vector is at a sufficiently small distance from another person's vector then the affect aggregator 340 will look for other content that has been liked or smiled at. This other content may be recommended by the recommendation engine 360 to the person 310 because there are assumed similarities based on the affect data which was collected.

In some embodiments, the affect aggregator 340 and affect analyzer 350 may be used to review affect data stored in the affect repository to compare affect data collected on a new video with an historical database of affect data for videos. The new video may be evaluated to determine how this video ranks against other videos. For example, the new video could be compared with a "top 100" list of videos to determine the relative number of smiles that the new video has relative to the "top 100" list of videos for which people smiled. In embodiments, a group of people can view a new video and have affect data collected. The affect data collected for the people could be aggregated together. The aggregated affect data for the new video could then be compared to the aggregated affect data for other videos. This type of comparison could be used by developers of videos to rank and evaluate a new video which has been produced. Likewise a buyer of advertising spots, for example, could evaluate a new video based on aggregated affect data collected from a group of people. For certain purposes an emotion profile could be generated and then compared with a "best of breed" set of videos by network studios, advertisers, or others with similar commercial interest.

In some cases there may be good correlation for one type of video but not another. For instance, a good correlation may be made for drama videos but a poor one for comedy video. Based on that information, a recommendation may be made for another drama video. Collaborative filtering may be performed to identify good possibilities for correlation and therefore areas where videos may be recommended.

The recommendation engine 360 may make recommendations to the person 310 on whom affect was collected. The recommendation engine 360 may make these recommendations based on the correlation between the person 310 and the other people 322. Likewise, the recommendation engine 360 may make recommendations to one or more of the people 322 based on a video that was viewed by the person 310.

Figure 4:
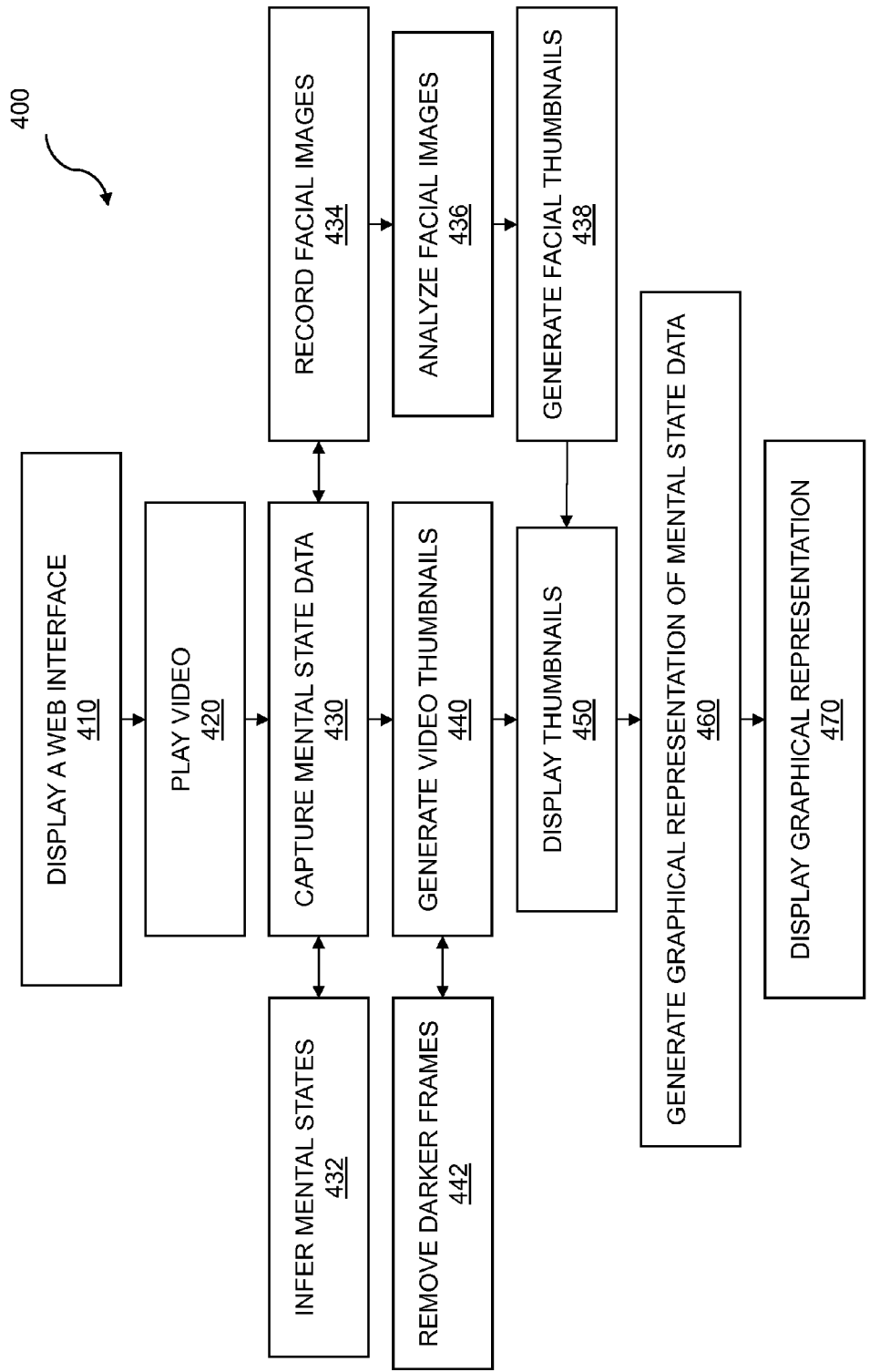
FIG. 4 is a flow diagram for displaying affect.

FIG. 4 is a flow diagram for displaying affect. The flow 400 describes a computer-implemented method for displaying affect. The flow 400 may begin with displaying a first web-enabled interface 410. The first web-enabled interface may include a web page. The flow 400 may continue with playing a video 420 on the first web-enabled interface. The video may include a YouTube™ or a Vimeo™ video. The video may be one of a group consisting of a movie, a television show, a web series, a webisode, a video, a video clip, or may be media such as an electronic game, an advertisement, an e-book, an e-magazine, or a movie trailer. The flow 400 may continue with capturing mental state data 430 while the video is played. The flow may further comprise inferring of mental states 432 based on the mental state data which was collected. The mental states may include one of a group consisting of frustration, confusion, disappointment, hesitation cognitive overload, focusing, being engaged, attending, boredom, exploration, confidence, trust, delight, valence, skepticism, and satisfaction.

The capturing mental state data may further comprise recording facial images 434. The flow 400 may further comprise analyzing the facial images for a facial expression 436. The facial data may include information on one or more of a group consisting of facial expressions, action units, head gestures, smiles, brow furrows, squints, lowered eyebrows, raised eyebrows, smirks, attention, and the like. The facial expressions may be used to generate facial thumbnails 438. In some embodiments, representative low-resolution images may be included in the thumbnails rather than images obtained directly from a webcam or other imaging apparatus.

The flow 400 may continue with generating a set of thumbnails 440 for the video which was played, where the thumbnails comprise scenes from the video and the set of thumbnails may be generated automatically. The flow 400 may further comprise analyzing the set of thumbnails and removing a frame from the set of thumbnails based on a dark threshold. Another frame may be used in place of the frame that was removed. The flow 400 may continue with displaying the set of thumbnails 450 on a second web-enabled interface. The second web-enabled interface may include a web page. In embodiments, the thumbnails will be for the video which was played.

In embodiments, an individual thumbnail is one "scene" from the video and is a static image of a specified size. Various items can be useful in the generation of thumbnails and are briefly discussed here. A composite of thumbnails or zoetrope is a horizontal array of images. A dark threshold is used to analyze a mean value of the color of an image to determine whether it is "dark." A starting offset is a number of seconds into the video to begin the thumbnail generation process. A number of seconds between frames can be automatically generated or specified manually and refers to the number of seconds between the individual thumbnail images. A zoetrope width is the width of the final image and may be slightly different from the width of an individual thumbnail multiplied by the number of thumbnails. A size string may be of the form "width times height" and examples include 24×24, 32×32, 40×32, etc. The size string determines the dimensions of the individual thumbnail. The individual thumbnails may be examined to determine if the image is "too dark." Some movie trailers frequently fade to black. Black or very dark frames often make for poor thumbnails. A recursive look forward and backward to find a better frame is possible. If a frame is too dark, then the recursive algorithm looks behind and forward by small amounts to see if it can find a better frame that can be found within certain recursion limits. Once a good image is found or a recursion limit is reached, the video is advanced by the appropriate number of seconds between frames to identify the next thumbnail image.

In some embodiments, the flow 400 may further comprise generating a set of thumbnails for the facial images which were recorded 438 and displaying the set of thumbnails 450 for the facial images on the second web-enabled interface. One thumbnail from the set of thumbnails may be selected based on a facial expression. The one thumbnail may show an animated facial expression. The one thumbnail may show an unusual facial expression. The one thumbnail may show a typical facial expression.

The flow 400 may continue with generating a graphical representation of the mental state data 460 which was captured. The graphical representation may be a line graph showing an amount of a specific mental state or an amount of a specific facial expression. Likewise the graphical representation may be a more complex dashboard-type presentation. The flow 400 may continue with displaying the graphical representation 470 on the second web-enabled interface. The graphical representation may include a score representing the mental state data. The score may be for a specific mental state, such as attention, frustration, disappointment, or any other mental state. The score may provide a numerical representation of the mental state.

In some embodiments, the playing of the video is done on a mobile device and the recording of the facial images is done with the mobile device. In embodiments, the mental state data is captured from multiple people and aggregated. Various steps in the flow 400 may be changed in order, repeated, omitted, or the like without departing from the disclosed inventive concepts. Various embodiments of the flow 400 may be included in a computer program product embodied in a non-transitory computer readable medium that includes code executable by one or more processors.

Figure 5:
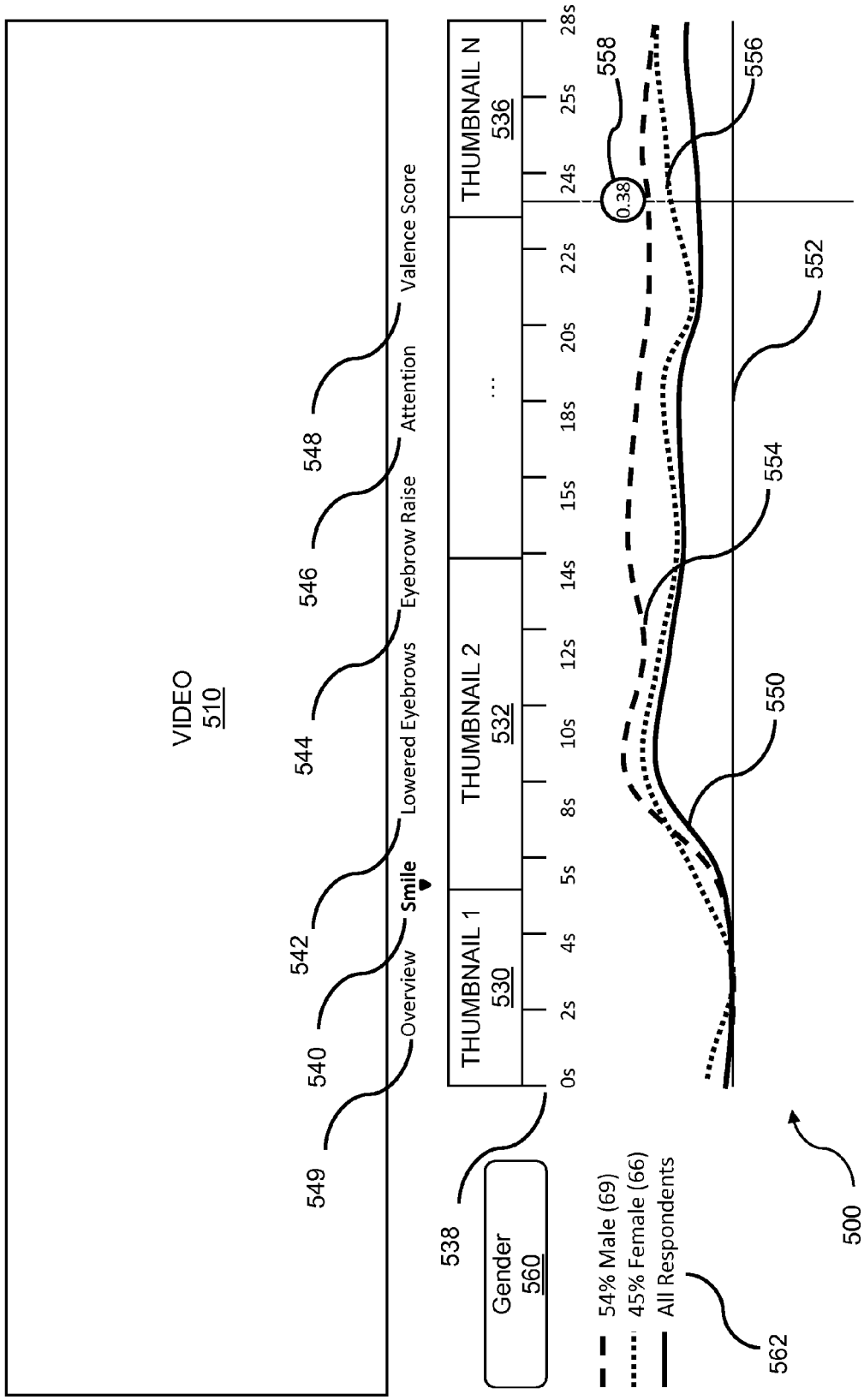
FIG. 5 is a graphical representation of displaying affect.

FIG. 5 is a graphical representation of displaying affect. Display, or dashboard, 500 is a graphical representation of mental state analysis that may be shown for video viewer analysis and may be presented on an electronic display. The display may be a television monitor, projector, computer monitor (including a laptop screen, a tablet screen, a netbook screen, and the like), a cell phone display, a mobile device, or other electronic display. In embodiments, the display may be a webpage. An example window 500 is shown which includes, for example, a rendering of a video 510 along with associated mental state information. The visualization may further comprise the rendering related to the video 510. A user may be able to select among a plurality of video renderings using various buttons and/or tabs. The user interface allows a plurality of parameters to be displayed as a function of time, synchronized to the video rendering 510. Various embodiments may have any number of selections available for the user, and some may include other types of renderings instead of video. A set of thumbnail images for the selected rendering, that in the example shown, include Thumbnail 1 530, Thumbnail 2 532, through Thumbnail N 536 which may be shown below the rendering along with a timeline 538. The thumbnails may show a graphic "storyboard" of the video rendering. This storyboard may assist a user in identifying a particular scene or location within the video rendering. Some embodiments may not include thumbnails, or may have a single thumbnail associated with the rendering, while various embodiments may have thumbnails of equal length and others may have thumbnails of differing lengths. In some embodiments, the start and/or end of the thumbnails may be determined based on changes in the captured viewer mental states associated with the rendering, or may be based on particular points of interest in the video rendering. Thumbnails of one or more viewers may be shown along the timeline 538. The thumbnails of viewers may include peak expressions, expressions at key points in the video rendering 510, etc.

Some embodiments may include the ability for a user to select a particular type of mental state information for display using various buttons or other selection methods. The mental state information may be based on one or more descriptors. The one or more descriptors may include, but are not limited to, one of action unit 4 (AU4), action unit 12 (AU12), and valence. By way of example, in the window 500, the smile mental state information is shown as the user may have previously selected the Smile button 540. Other types of mental state information that may be available for user selection in various embodiments may include the Lowered Eyebrows button 542, Eyebrow Raise button 544, Attention button 546, Valence Score button 548, or other types of mental state information, depending on the embodiment. An Overview button 549 may be available to allow a user to show graphs of the multiple types of mental state information simultaneously. The mental state information may include probability information for one or more descriptors, and the probabilities for the one of the one or more descriptors may vary for portions of the video rendering.

Because the Smile option 540 has been selected in the example shown, smile graph 550 may be shown against a baseline 552, showing the aggregated smile mental state information of the plurality of individuals from whom mental state data was collected for the video. The male smile graph 554 and the female smile graph 556 may be shown so that the visual representation displays the aggregated mental state information. These graphs are provided by way of example only. The mental state information may be based on a demographic basis as those viewers who comprise that demographic react to the video. The various demographic based graphs may be indicated using various line types as shown or may be indicated using color or other method of differentiation. A slider 558 may allow a user to select a particular time of the timeline and show the value of the chosen mental state for that particular time. The video 510 may be coordinated with the slider 558. The slider 558 may be selected and moved with a mouse or other pointing device in some embodiments. The video 510 may jump to the point in time to which the slider 558 has been moved. The mental states can be used to evaluate the value of the video.

Various types of demographic-based mental state information may be selected using the demographic button 560 in some embodiments. Such demographics may include gender, age, race, income level, education, or any other type of demographic including dividing the respondents into those respondents that had higher reactions from those with lower reactions. A graph legend 562 may be displayed indicating the various demographic groups, the line type or color for each group, the percentage of total respondents and/or absolute number of respondents for each group, and/or other information about the demographic groups. The mental state information may be aggregated according to the demographic type selected. Thus, aggregation of the mental state information is performed on a demographic basis so that mental state information is grouped based on the demographic basis, for some embodiments. The video thus may be evaluated for responses by various demographic groups.

Figure 6:
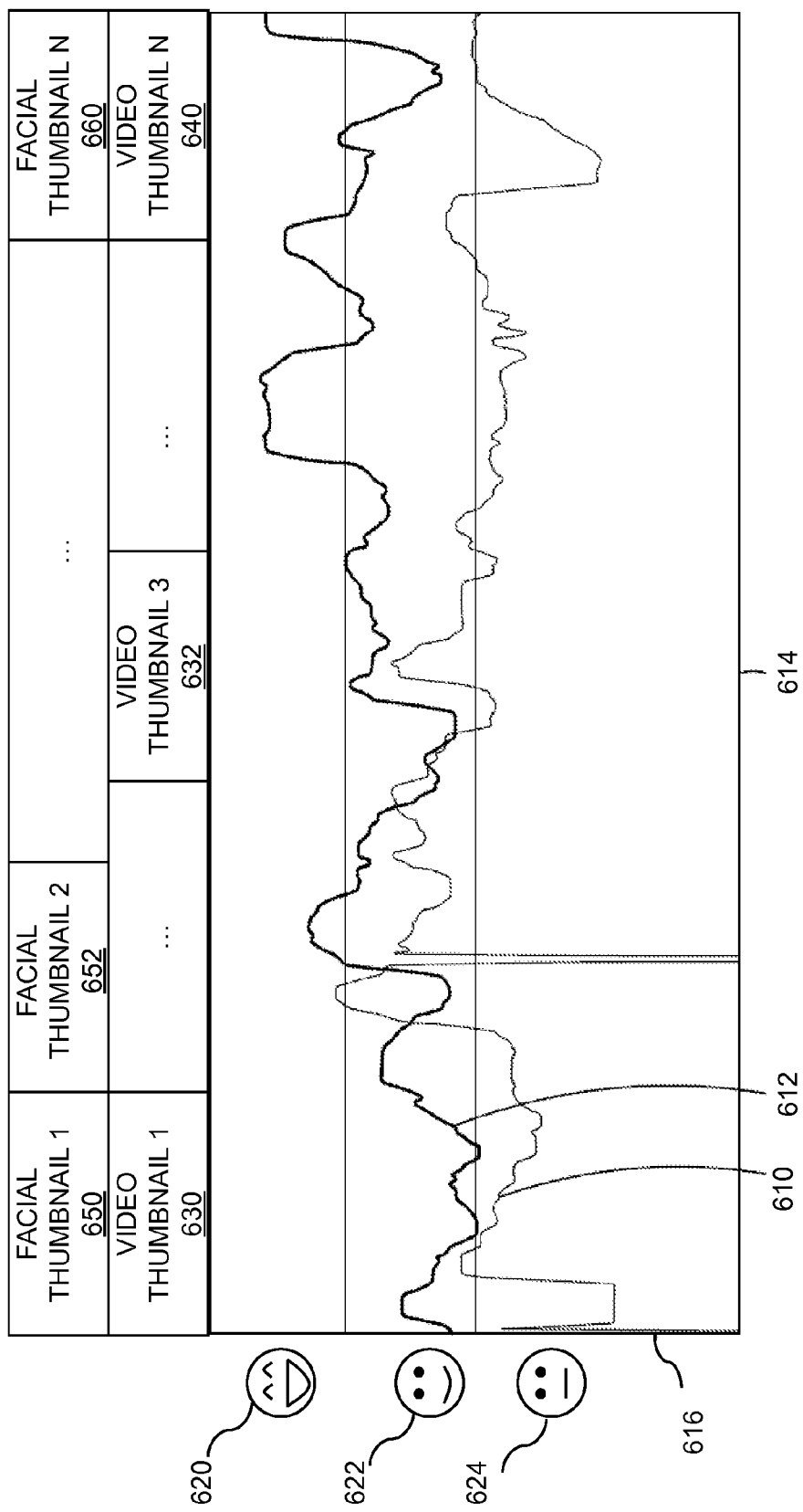
FIG. 6 is a graphical representation for displaying aggregated affect.

FIG. 6 is a graphical representation for displaying affect based on mental state analysis along with an aggregated result from a group of people. This rendering may be displayed on a web page, web enabled application, a dashboard, or other type of electronic display representation. A graph 610 may be shown for an individual on whom affect data is collected. Another graph 612 may be shown for affect collected on another individual or aggregated affect from multiple people. The mental state analysis may be based on facial image or physiological data collection. In some embodiments, the graph 610 may indicate the amount or probability of a smile being observed for the individual. A higher value or point on the graph may indicate a stronger or larger smile. In certain spots the graph may drop out or degrade when image collection was lost or was not able to identify the face of the person. The probability or intensity of an affect may be given along the y-axis 616. A timeline may be given along the x-axis 614. The aggregated information may be based on taking the average, median, or other statistical or calculated value based on the information collected from a group of people. In some embodiments, combination of the aggregated mental state information is accomplished using computational aggregation.

In some embodiments, graphical smiley face icons 620, 622, and 624 may be shown providing an indication of the amount of a smile or other facial expression. A first very broad smiley face icon 620 may indicate a very large smile being observed. A second normal smiley face icon 622 may indicate a smile being observed. A third face icon 624 may indicate no smile. The icons may correspond to a region on the y-axis 616 that indicate the probability or intensity of a smile.

A set of facial thumbnail images related to the selected graph or graphs, that in the example shown, include Facial Thumbnail 1 650, Facial Thumbnail 2 652, through Facial Thumbnail N 660, may be shown above or below the graph, and may be displayed with a timeline or other parameter along the x-axis 614. The thumbnails may show a graphic "storyboard" of the facial rendering. This storyboard may assist a user in identifying a particular scene or location within the facial rendering. Some embodiments may not include thumbnails, or may have a single thumbnail associated with the facial rendering, while various embodiments may have thumbnails of equal length while others may have thumbnails of differing lengths. In some embodiments, the start and/or end of the thumbnails may be determined based on changes in the captured viewer mental states associated with the rendering, or may be based on particular points of interest in the video rendering. Thumbnails of one or more viewers may be shown along a timeline or other parameter 614. The thumbnails of viewers may include peak expressions, expressions at key points in the video rendering, key points in the graphs, etc.

A set of video thumbnail images comprising scenes from the video for the selected graph or graphs, that in the example shown, include Video Thumbnail 1 630, Video Thumbnail 2 632, through Video Thumbnail N 640, may be shown above or below the graph, and may be displayed with a timeline or other parameter along the x-axis 614. The thumbnails may show a graphic "storyboard" of the video rendering. This storyboard may assist a user in identifying a particular scene or location within the video rendering. Some embodiments may not include thumbnails, or may have a single thumbnail associated with the rendering, while various embodiments may have thumbnails of equal length while others may have thumbnails of differing lengths. In some embodiments, the start and/or end of the thumbnails may be determined based on changes in the captured viewer mental states associated with the rendering, or may be based on particular points of interest in the video rendering.

Figure 7:
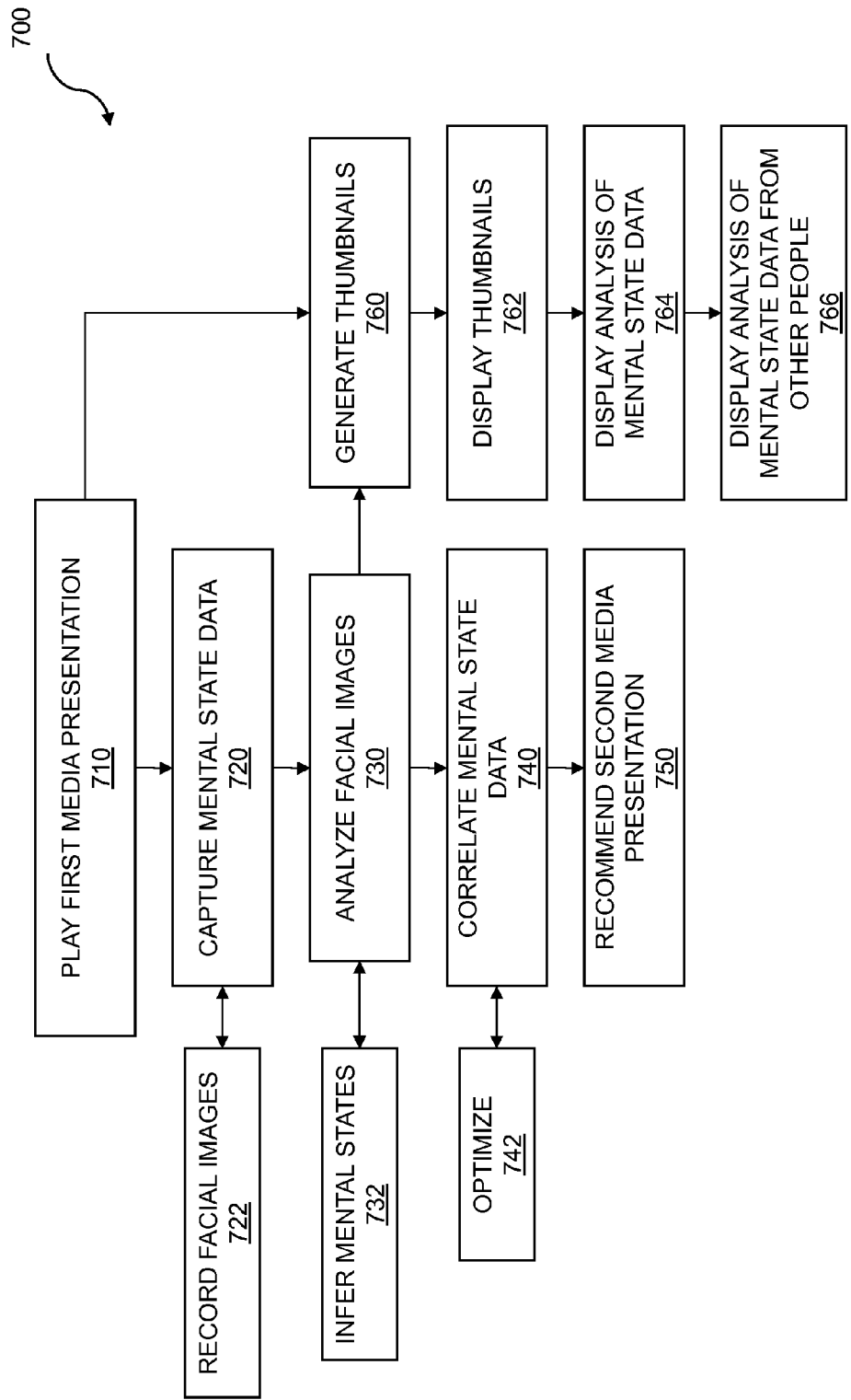
FIG. 7 is a flow diagram for affect-based recommendations.

FIG. 7 is a flow diagram for affect-based recommendations. A flow 700 describes a computer-implemented method for affect-based recommendations. The flow 700 may begin with playing a first media presentation 710 to an individual. The first media presentation may be one of a group consisting of a movie, a television show, a web series, a webisode, a video, a video clip, an electronic game, an e-book, and an e-magazine, or other media object. The first media presentation may include a YouTube™ video, a Vimeo™ video, or a Netflix™ video. The first media presentation may be played on a web-enabled interface or other electronic display interface. The web-enabled interface may include a web page. The playing of the first media presentation may be done on a mobile device. The flow 710 may continue with capturing mental state data 720 for the individual while the first media presentation is played. The mental state data collected may include physiological data, facial data, actigraphy data, and the like. The capturing of mental state data may further comprise recording facial images 722. Capture of the facial image may be realized by a webcam or other camera. The playing of the first media presentation may be done on a mobile device and the recording of the facial images may also be done with the mobile device. The recording of facial images 722 with the mobile device may be part of the capturing of mental state data. The flow 700 may further comprise analyzing the facial images 730 for a facial expression. The facial expression may include a smile. The facial expression may include a brow furrow. The analyzing facial images may further comprise using the facial images to infer mental states 732. The mental states may include frustration, confusion, disappointment, hesitation, cognitive overload, focusing, being engaged, attending, boredom, exploration, confidence, trust, delight, satisfaction, valence, skepticism, happiness, and the like.

The flow 700 may continue with correlating the mental state data 740 which was captured for the individual to mental state data collected from other people who experienced the first media presentation. The correlating may include identifying similar likes and dislikes as well as similar various other mental states. In some embodiments, distributions of responses to various videos may be correlated. In other embodiments, differences may be correlated, such as, for example, identifying maximally dissimilar responses. In some embodiments, certain mental states may be identified as being similar while others are identified as being dissimilar during part of the correlation. The flow 700 may include optimizing 742 the media presentation based on the mental state data. The optimizing 742 may include modifying content or recommending changes in content, such as eliminating scenes, reducing certain material, or emphasizing certain actors. In embodiments, the media presentation includes a mixture of advertising and content. The optimizing 742 may select one or more advertisements to be interspersed with the content. The optimizing 742 may include ordering one or more advertisements to be interspersed with the content. The optimizing 742 may include selecting times within the content for playing the one or more advertisements. The optimizing 742 may include identifying portions of an advertisement that are removed to form a shortened advertisement.

The flow 700 may include recommending a second media presentation 750 to the individual based on the mental state data which was captured for the individual. The recommending the second media presentation to the individual may be based on the correlating between the individual and the other people. The second media presentation may be one of a group consisting of a movie, a television show, a web series, a webisode, a video, a video clip, an electronic game, an e-book, and an e-magazine, and the like. The second media presentation may include a YouTube™ video, a Vimeo™ video, or a Netflix™ video.

The flow 700 may further comprise generating a set of thumbnails 760 for the first media presentation which was played and displaying the set of thumbnails 762 on a second web-enabled interface or digital display along with an analysis of the mental state data from the individual 764. The set of thumbnails may comprise scenes from the first media presentation. The selection of the thumbnail from the set of thumbnails may be based on facial expression. The set of thumbnails may be generated automatically and may include removing a frame from the set of thumbnails based on a dark threshold. Another frame may be used in place of the frame that was removed. The flow 700 may further comprise displaying an analysis of the mental state data from the other people 766. Various steps in the flow 700 may be changed in order, repeated, omitted, or the like without departing from the disclosed inventive concepts. Various embodiments of the flow 700 may be included in a computer program product embodied in a non-transitory computer readable medium that includes code executable by one or more processors.

Figure 8:
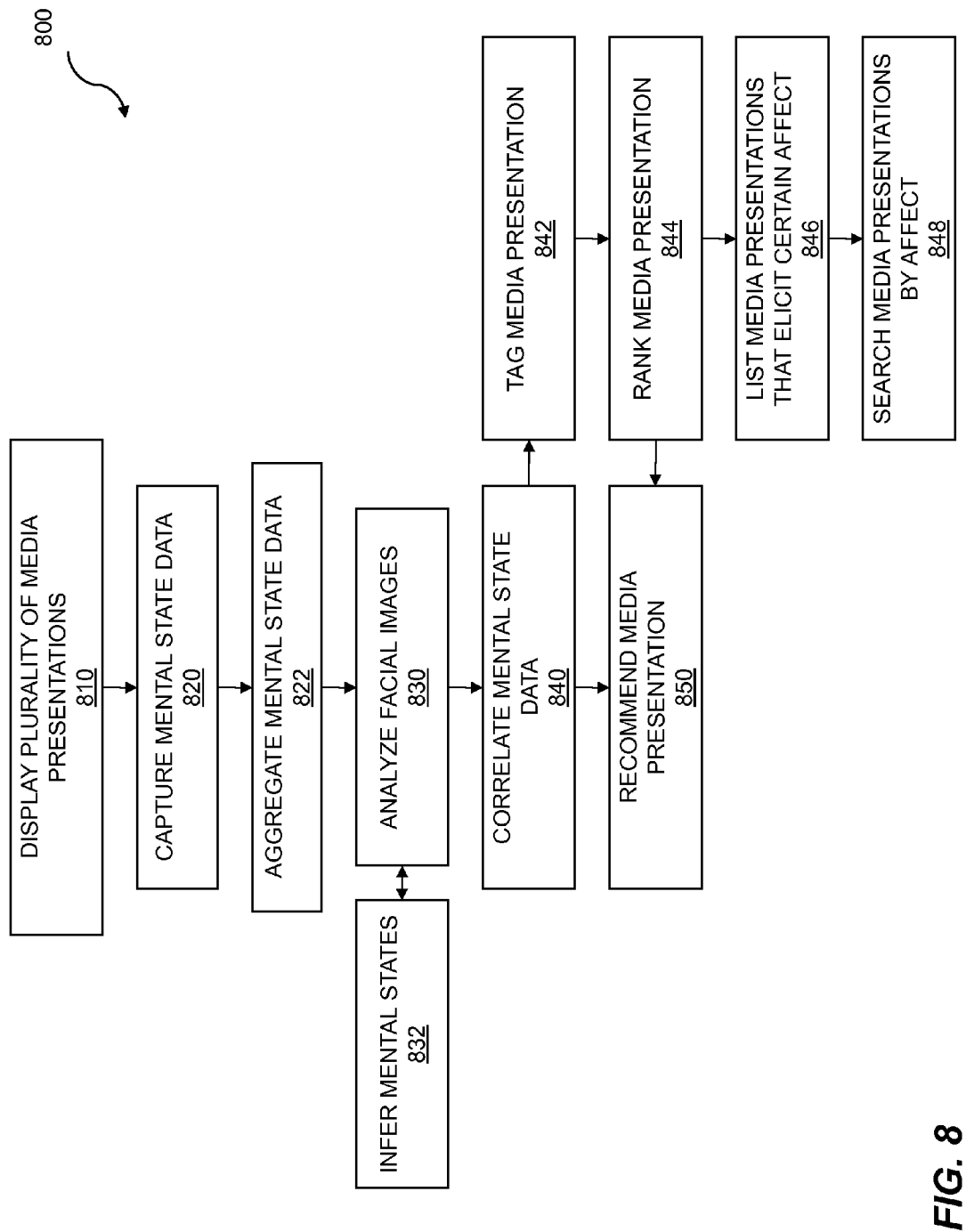
FIG. 8 is a flow diagram for affect-based video ranking.

FIG. 8 is a flow diagram for affect-based video ranking and includes a flow 800 which describes a computer-implemented method for affect-based ranking. The flow 800 may begin with displaying a plurality of media presentations 810 to a group of people. The plurality of media presentations may include videos. The plurality of videos may include YouTube™ videos, Vimeo™ videos, or Netflix™ videos. Further, the plurality of media presentations may include one of a group consisting of a movie, a movie trailer, a television show, a web series, a webisode, a video, a video clip, an advertisement, a music video, an electronic game, an e-book, and an e-magazine. The flow 800 may continue with capturing mental state data 820 from the group of people while the plurality of media presentations is displayed. Thus, mental state data may be captured from multiple people. The affect data may include facial images. In some embodiments, the playing of the media presentations is done on a mobile device and the recording of the facial images is done with the mobile device. The flow 800 may include aggregating the mental state data 822 from the multiple people. The flow 800 may further comprise analyzing the facial images 830 for a facial expression. The facial expression may include a smile. The facial expression may include a brow furrow. The flow 800 may further comprise using the facial images to infer mental states 832. The mental states may include one of a group consisting of frustration, confusion, disappointment, hesitation, cognitive overload, focusing, being engaged, attending, boredom, exploration, confidence, trust, delight, valence, skepticism, satisfaction, and the like.

The flow 800 may include correlating the mental state data 840 captured from the group of people who have viewed the plurality of media presentations and had their mental state data captured. The plurality of videos viewed by the group of people may have some common videos seen by each of the people in the group of people. In some embodiments, the plurality of videos may not include an identical set of videos. The flow 800 may continue with tagging the plurality of media presentations 842 with mental state information based on the mental state data which was captured. The affect information may simply be the affect data. In other embodiments, the affect information may be the inferred mental states. In still other embodiments the affect information may be results of the correlation. The flow 800 may continue with ranking the media presentations 844 relative to another media presentation based on the mental state data which was collected. The ranking may be for an individual based on the mental state data captured from the individual. The ranking may be based on anticipated preferences for the individual. In some embodiments, the ranking of a first media presentation relative to another media presentation may be based on the mental state data which was aggregated from multiple people. The ranking may also be relative to media presentations previously stored with affect information. The ranking may include ranking a video relative to another video based on the mental state data which was captured. The flow 800 may further comprise displaying the videos which elicit a certain affect 846. The certain affect may include one of a group consisting of smiles, engagement, attention, interest, sadness, liking, disliking, and so on. The ranking may further comprise displaying the videos which elicited a larger number of smiles. As a result of ranking, the media presentations may be sorted based on which are funniest, saddest, generate the most tears, or engender some other response. The flow 800 may further comprise searching through the videos based on a certain affect data 848. A search 848 may identify videos which are very engaging, funny, sad, poignant, or the like.

The flow 800 may include recommending a second media presentation 850 to an individual based on the affect data that was captured and based on the ranking. The second media presentation may be one of a group consisting of a movie, a movie trailer, a television show, a web series, a webisode, a video, a video clip, an advertisement, a music video, an electronic game, an e-book, and an e-magazine.

Based on the mental states, recommendations to or from an individual may be provided. One or more recommendations may be made to the individual based on mental states, affect, or facial expressions. A correlation may be made between one individual and others with similar affect exhibited during multiple videos. The correlation may include a record of other videos, games, or other experiences along with their affect. Likewise a recommendation for a movie, video, video clip, webisode or other activity may be made to individual based on their affect. Various steps in the flow 800 may be changed in order, repeated, omitted, or the like without departing from the disclosed inventive concepts. Various embodiments of the flow 800 may be included in a computer program product embodied in a non-transitory computer readable medium that includes code executable by one or more processors.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from any number of viewers who are online. That is, the collection of videos can be crowdsourced from those viewers who elected to opt-in to the video data collection.

In some embodiments, a high frame rate camera may be used. A high frame rate camera has a frame rate of 60 frames per second or higher. With such a frame rate, micro expressions may also be captured. Micro expressions are very brief facial expressions, lasting only a fraction of a second. They occur when a person either deliberately or unconsciously conceals a feeling.

In some cases, micro expressions happen when people have hidden their feelings from themselves (repression) or when they deliberately try to conceal their feelings from others. In some cases, the micro expressions may only last about 50 milliseconds. Hence, these expressions may go unnoticed by a human observer. However, a high frame rate camera may be used to capture footage at a sufficient frame rate such that the footage can be analyzed for the presence of micro expressions. Micro expressions may be analyzed via action units as previously described, with various attributes such as brow raising, brow furls, eyelid raising, and the like. Thus, embodiments may analyze micro expressions that are easily missed by human observers due to their transient nature.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include such items as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. For example, the AUs can be used to recognize emotions experienced by the observed person. Emotion-related facial actions can be identified using the emotional facial action coding system (EM-FACS) and the facial action coding system affect interpretation dictionary (FACSAID), for example. For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated as well as specific emotions, moods, or mental states.

The coding of faces identified in videos captured of people observing an event can be automated. The automated systems can detect facial AUs or discrete emotional states. The emotional states can include amusement, fear, anger, disgust, surprise, and sadness, for example. The automated systems can be based on a probability estimate from one or more classifiers, where the probabilities can correlate with an intensity of an AU or an expression. The classifiers can be used to identify into which of a set of categories a given observation can be placed. For example, the classifiers can be used to determine a probability that a given AU or expression is present in a given frame of a video. The classifiers can be used as part of a supervised machine learning technique where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. For example, the image can be adjusted by flipping the image around a vertical line through the middle of a face in the image. The symmetry plane of the image can be determined from the tracker points and landmarks of the image.

In an embodiment, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions, and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis.

Figure 9:
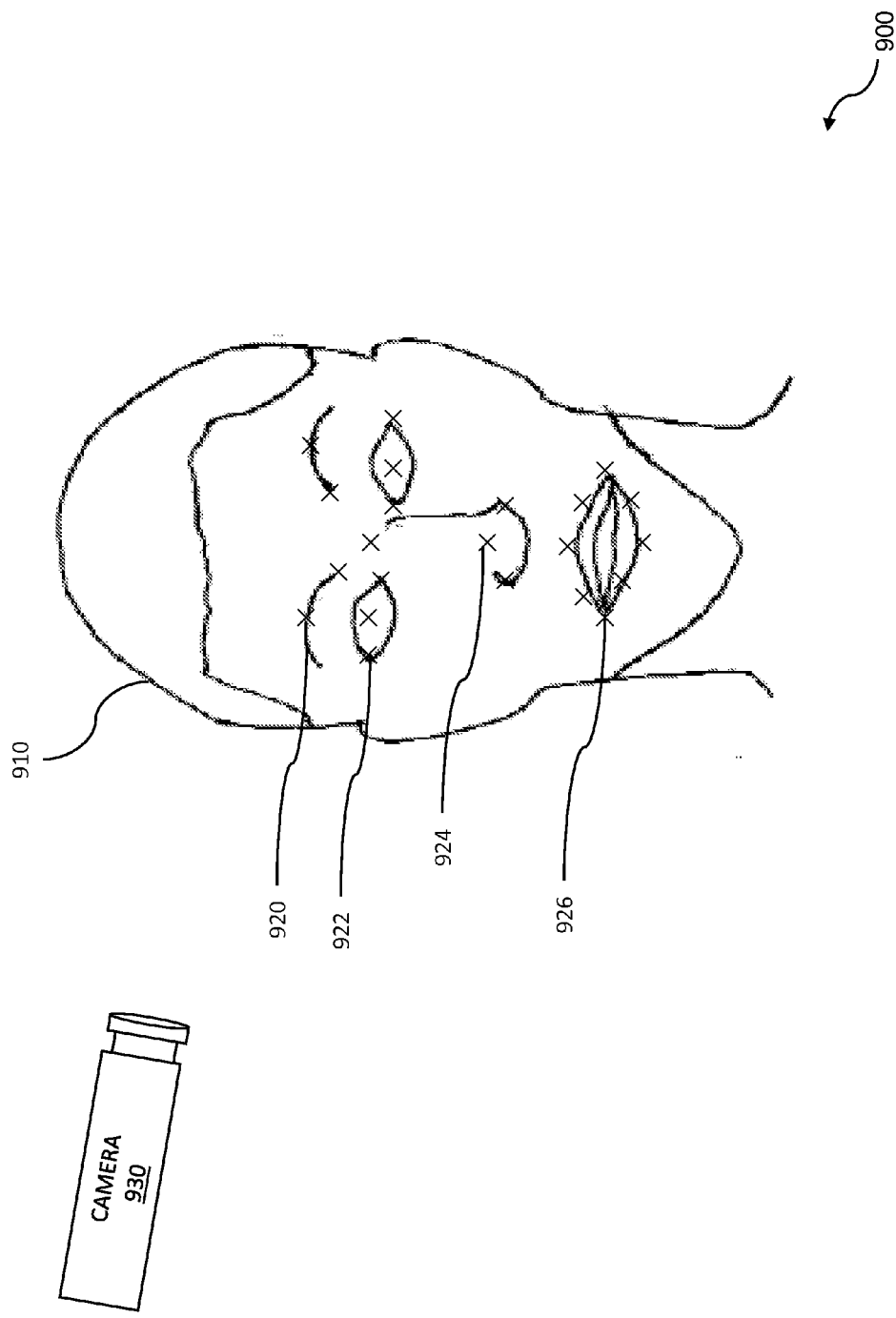
FIG. 9 shows example facial data collection including landmarks.

FIG. 9 shows a diagram 900 illustrating example facial data collection including landmarks. A face 910 can be observed using a camera 930 in order to collect facial data that includes facial landmarks. The facial data can be collected from a plurality of people using one or more of a variety of cameras. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend, for example, on the position of the camera 930 relative to the face 910, the number of cameras used, the illumination of the face, etc. For example, if the face 910 is poorly lit or over-exposed (e.g. in an area of bright light), the processing of the facial data to identify facial landmarks might be rendered more difficult. In another example, the camera 930 being positioned to the side of the person might prevent capture of the full face. Other artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 920, an outer eye edge 922, a nose 924, a corner of a mouth 926, and so on. Any number of facial landmarks can be identified from the facial data that is captured. The facial landmarks that are identified can be analyzed to identify facial action units. For example, the action units that can be identified include AU02 outer brow raiser, AU14 dimpler, AU17 chin raiser, and so on. Any number of action units can be identified. The action units can be used alone and/or in combination to infer one or more mental states and emotions. A similar process can be applied to gesture analysis (e.g. hand gestures).

Figure 10:
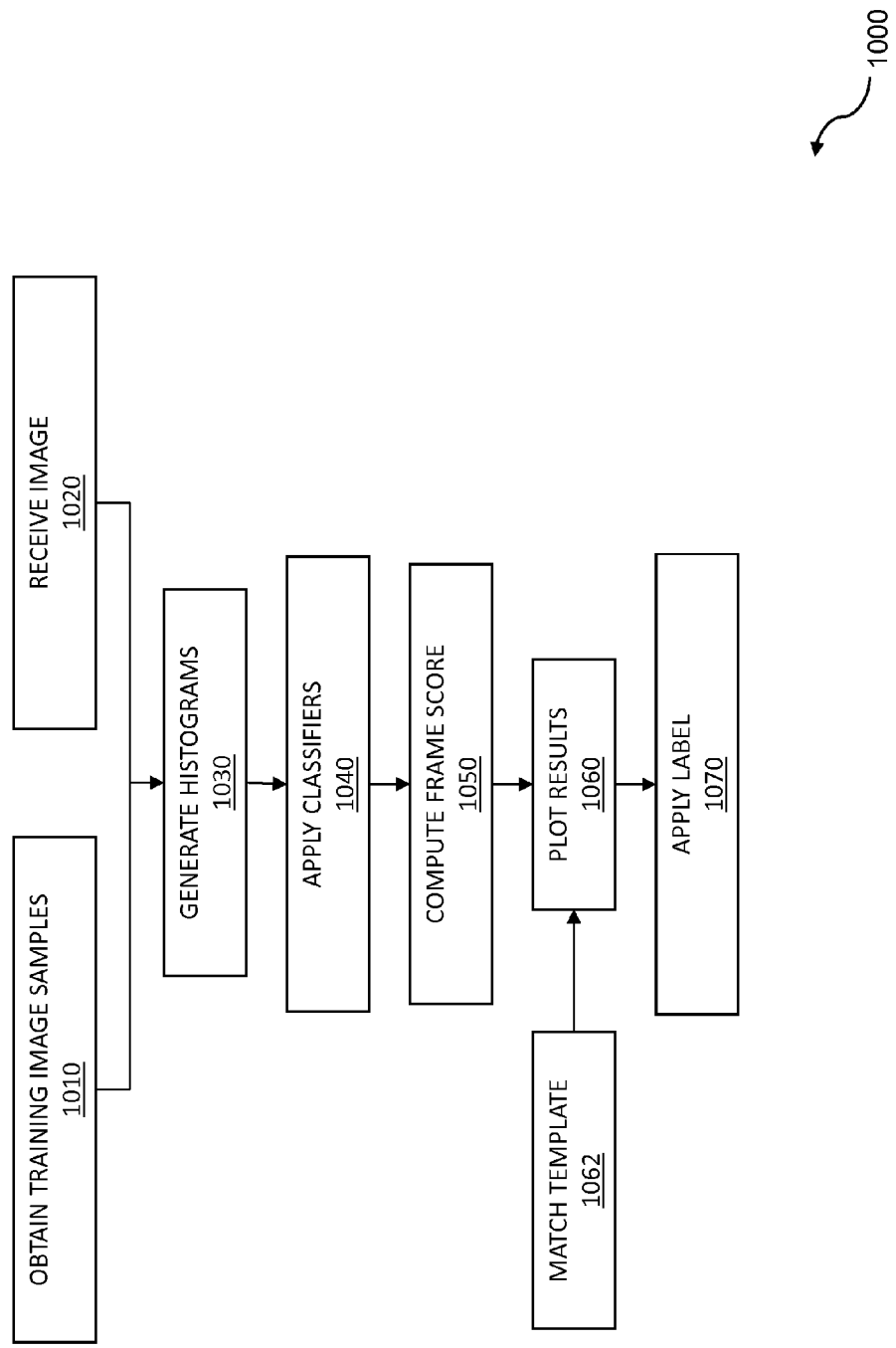
FIG. 10 is a flow diagram for detecting facial expressions.

FIG. 10 is a flow for detecting facial expressions. The flow 1000 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU) where the action units are determined using FACS coding. The AIls can be used singly or in combination to identify facial expressions. Based on the facial landmarks, one or more AUs can be identified by number and intensity. For example, AU12 can be used to code a lip corner puller and can be used to infer a smirk.

The flow 1000 begins by obtaining training image samples 1010. The image samples can include a plurality of images of one or more people. Human coders who are trained to correctly identify AU codes based on the FACS can code the images. The training or "known good" images can be used as a basis for training a machine learning technique. Once trained, the machine learning technique can be used to identify AUs in other images that can be collected using a camera, such as the camera 1230 from FIG. 4, for example. The flow 1000 continues with receiving an image 1020. The image 1020 can be received from the camera 1230. As discussed above, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image 1020 that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. For example, the manipulated image and a flipped or mirrored version of the manipulated image can be analyzed alone and/or in combination to improve analysis. The flow 1000 continues with generating histograms 1030 for the training images and the one or more versions of the received image. The histograms can be generated for one or more versions of the manipulated received image. The histograms can be based on a HoG or another histogram. As described above, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example.

The flow 1000 continues with applying classifiers 1040 to the histograms. The classifiers can be used to estimate probabilities where the probabilities can correlate with an intensity of an AU or an expression. The choice of classifiers used is based on the training of a supervised learning technique to identify facial expressions, in some embodiments. The classifiers can be used to identify into which of a set of categories a given observation can be placed. For example, the classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of any number of AUs can be determined. The flow 1000 continues with computing a frame score 1050. The score computed for an image, where the image can be a frame from a video, can be used to determine the presence of a facial expression in the image or video frame. The score can be based on one or more versions of the image 1020 or manipulated image. For example, the score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1000 continues with plotting results 1060. The results that are plotted can include one or more scores for one or frames computed over a given time t. For example, the plotted results can include classifier probability results from analysis of HoGs for a sequence of images and video frames. The plotted results can be matched with a template 1062. The template can be temporal and can be represented by a centered box function or another function. A best fit with one or more templates can be found by computing a minimum error. Other best-fit techniques can include polynomial curve fitting, geometric curve fitting, and so on. The flow 1000 continues with applying a label 1070. The label can be used to indicate that a particular facial expression has been detected in the one or more images or video frames which constitute the image 1020. For example, the label can be used to indicate that any of a range of facial expressions has been detected, including a smile, an asymmetric smile, a frown, and so on. Various steps in the flow 1000 may be changed in order, repeated, omitted, or the like without departing from the disclosed concepts. Various embodiments of the flow 1000 may be included in a computer program product embodied in a non-transitory computer readable medium that includes code executable by one or more processors.

Figure 11:
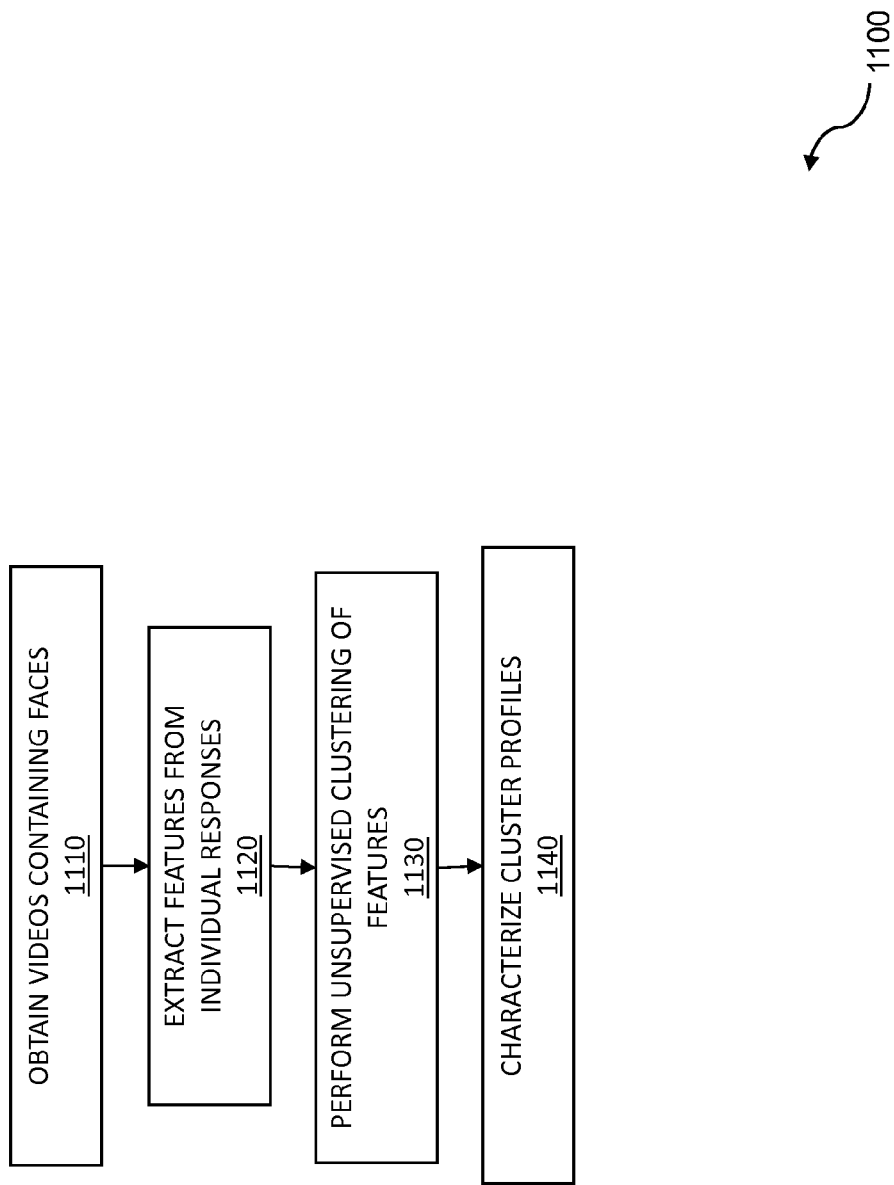
FIG. 11 is a flow diagram for large-scale clustering of facial events.

FIG. 11 is a flow 1100 for the large-scale clustering of facial events. As discussed above, collection of facial video data from one or more people can include a web-based framework. The web-based framework can be used to collect facial video data from, for example, large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from any number of viewers who are online. That is, the collection of videos can be crowdsourced from those viewers who elected to opt-in to the video data collection. The video event can be a commercial, a political ad, an educational segment, and so on. The flow 1100 begins with obtaining videos containing faces 1110. The videos can be obtained using one or more cameras, where the cameras can include a webcam coupled to one or more devices employed by the one or more people using the web-based framework. The flow 1100 continues with extracting features from the individual responses 1120. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1100 continues with performing unsupervised clustering of features 1130. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1100 continues with characterizing cluster profiles 1140. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. Similarly, the characterization can be performed on collected and analyzed videos of people viewing a news presentation. The characterized cluster profiles can be further analyzed based on demographic data. For example, the number of smiles resulting from people viewing a humorous video can be compared to various demographic groups, where the groups can be formed based on geographic location, age, ethnicity, gender, and so on. Various steps in the flow 1100 may be changed in order, repeated, omitted, or the like without departing from the disclosed concepts. Various embodiments of the flow 1100 may be included in a computer program product embodied in a non-transitory computer readable medium that includes code executable by one or more processors.

Figure 12:
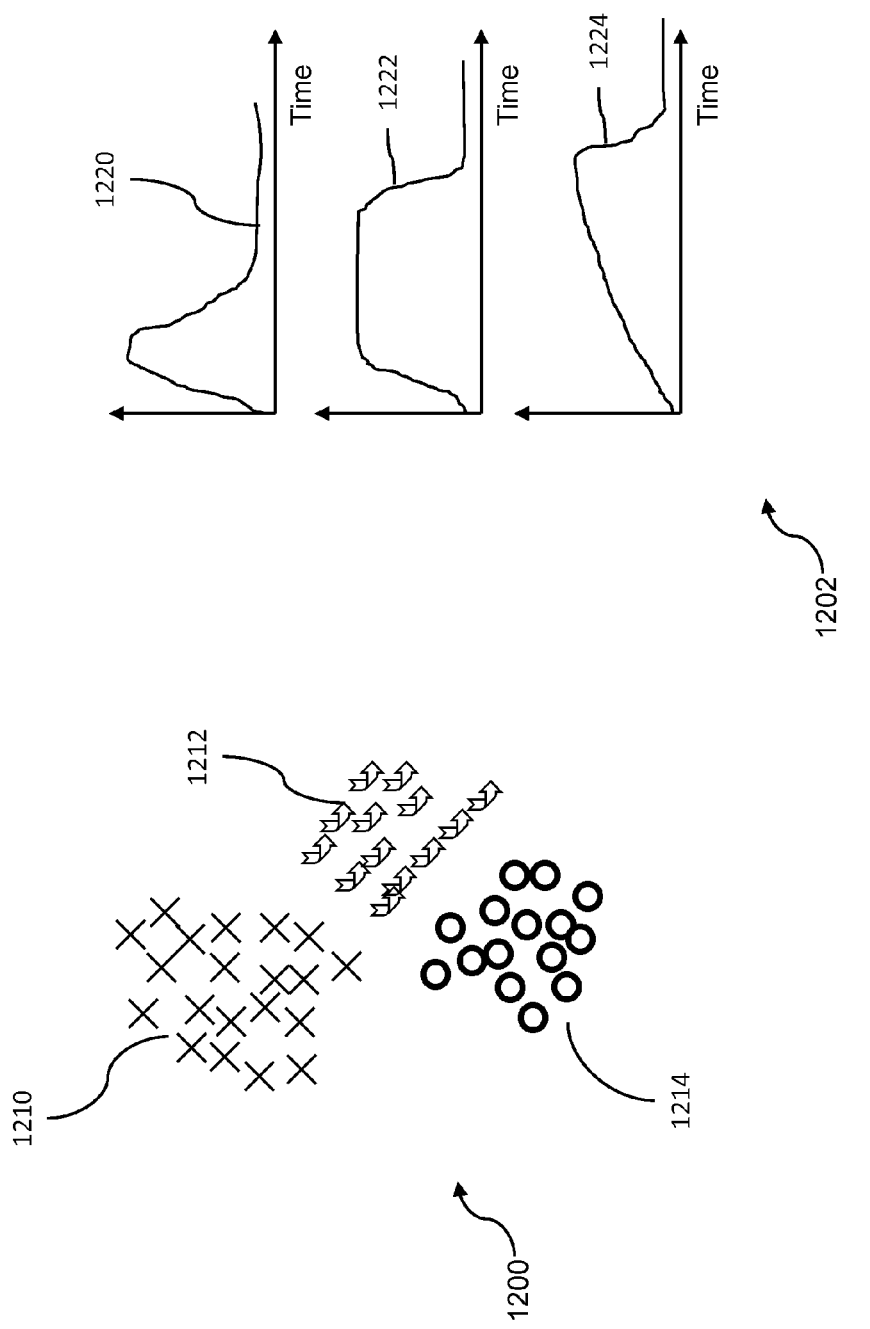
FIG. 12 shows example unsupervised clustering of features and characterizations of cluster profiles.

FIG. 12 shows example unsupervised clustering of features and characterization of cluster profiles. Features including samples of facial data can be clustered using unsupervised clustering. Various clusters can be formed, which include similar groupings of facial data observations. The example 1200 shows three clusters 1210, 1212, and 1214. The clusters can be based on video collected from people who have opted-in to video collection. When the data collected is captured using a web-based framework, then the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

Cluster profiles 1202 can be generated based on the clusters that can be formed from unsupervised clustering, with time shown on the x-axis and intensity or frequency shown on the y-axis. The cluster profiles can be based on captured facial data including facial expressions, for example. The cluster profile 1220 can be based on the cluster 1210, the cluster profile 1222 can be based on the cluster 1212, and the cluster profile 1224 can be based on the cluster 1214. The cluster profiles 1220, 1222, and 1224 can be based on smiles, smirks, frowns, or any other facial expression. Emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information as described above.

Figure 13A:
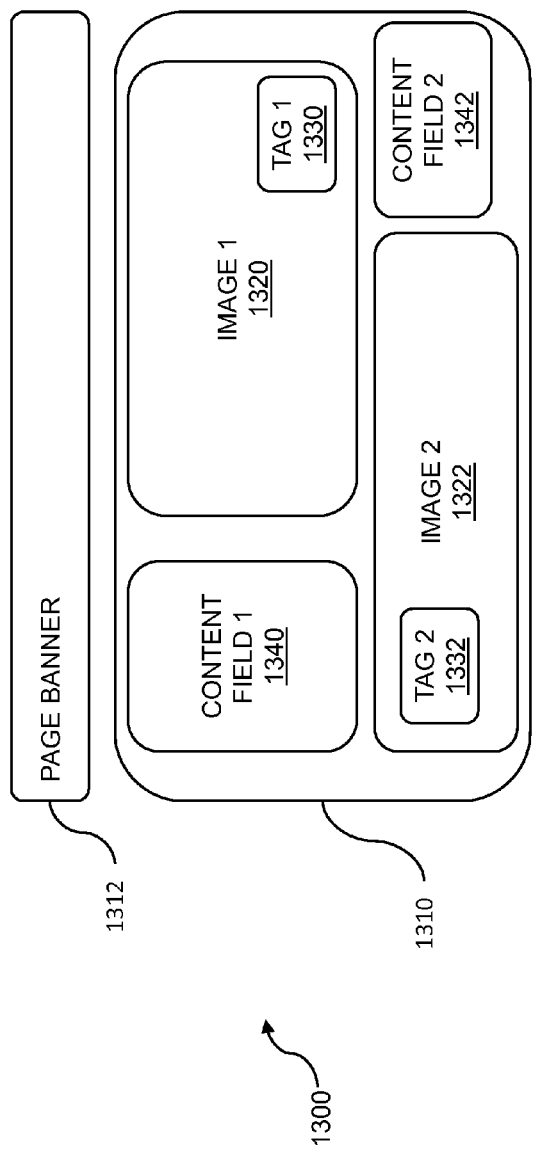
FIG. 13A shows example tags embedded in a webpage.

FIG. 13A shows example tags embedded in a webpage. A webpage 1300 can include a page body 1310, a page banner 1312, and so on. The page body can include one or more objects, where the objects can include text, images, videos, audio, and so on. The example page body 1310 shown includes a first image, image 1 1320; a second image, image 2 1322; a first content field, content field 1 1340; and a second content field, content field 2 1342. In practice, the page body 1310 can contain any number of images and content fields, and can include one or more videos, one or more audio presentations, and so on. The page body can include embedded tags, such as tag 1 1330 and tag 2 1332.

In the example shown, tag 1 1330 is embedded in image 1 1320, and tag 2 1332 is embedded in image 2 1322. In embodiments, any number of tags can be imbedded. Tags can also be imbedded in content fields, in videos, in audio presentations, etc. When a user mouses over a tag or clicks on an object associated with a tag, the tag can be invoked. For example, when the user mouses over tag 1 1330, tag 1 1330 can then be invoked. Invoking tag 1 1330 can include enabling a camera coupled to a user's device and capturing one or more images of the user as the user views a media presentation (or digital experience). In a similar manner, when the user mouses over tag 2 1332, tag 2 1332 can be invoked. Invoking tag 2 1332 can also include enabling the camera and capturing images of the user. In other embodiments, other actions can be taken based on invocation of the one or more tags. For example, invoking an embedded tag can initiate an analysis technique, post to social media, award the user a coupon or another prize, initiate mental state analysis, perform emotion analysis, and so on.

Figure 13B:
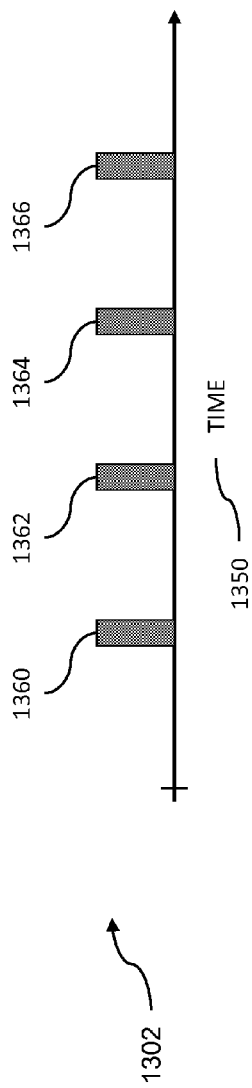
FIG. 13B shows example invoking tags for the collection of images.

FIG. 13B shows example tag invoking to collect images. As stated above, a media presentation can be a video, a webpage, and so on. A video 1302 can include one or more embedded tags, such as a tag 1360, another tag 1362, a third tag 1364, a fourth tag 1366, and so on. In practice, any number of tags can be included in the media presentation. The one or more tags can be invoked during the media presentation. The collection of the invoked tags can occur over time as represented by a timeline 1350. When a tag is encountered in the media presentation, the tag can be invoked. For example, when the tag 1360 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1360 does not enable the camera nor capture images of the user during the media presentation. The user can indicate an opt-in for certain types of participation, where opting-in can be dependent on specific content in the media presentation. For example, the user could opt-in to participation in a study of political campaign messages and not opt-in for a particular advertisement study. In this case, tags that are related to political campaign messages and that enable the camera and image capture when invoked would be embedded in the media presentation. However, tags imbedded in the media presentation that are related to advertisements would not enable the camera when invoked. Various other situations of tag invocation are possible.

Figure 14:
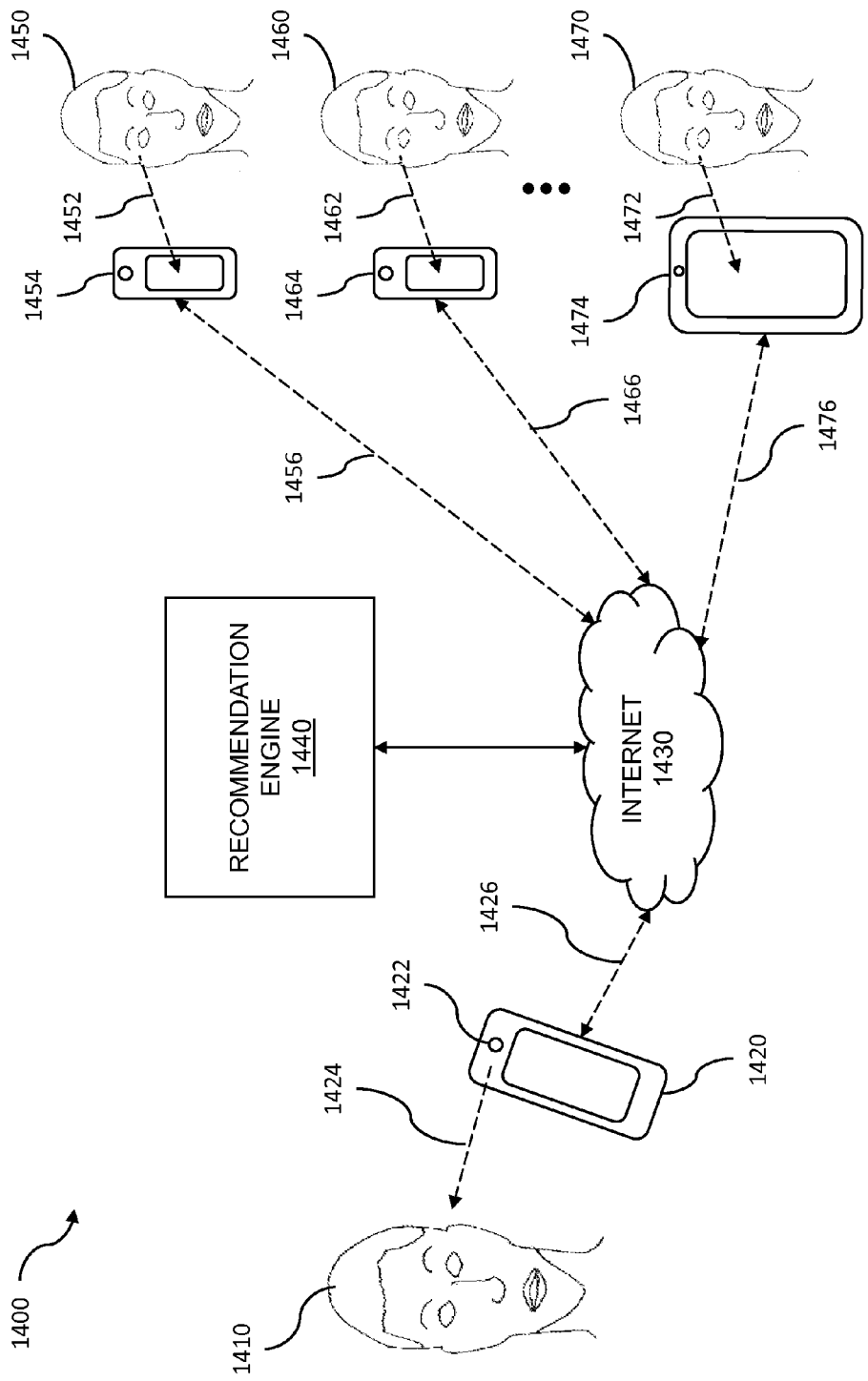
FIG. 14 shows an example live-streaming social video scenario.

FIG. 14 shows an example live-streaming social video scenario. Live-streaming video is an example of one-to-many social media where video can be sent over the Internet from one person to a plurality of people using a social media app and/or platform. Live-streaming is one of numerous popular techniques used by people who want to disseminate ideas, send information, provide entertainment, share experiences, and so on. Some of the live-streams can be scheduled, such as webcasts, online classes, sporting events, news, computer gaming, or videoconferences, while others can be impromptu streams that are broadcast as and when needed or desirable. Examples of impromptu live-stream videos can range from individuals simply wanting to share experiences with their social media followers, to coverage of breaking news, emergencies, or natural disasters. This latter coverage can be known as mobile journalism or "mo jo" and is becoming increasingly commonplace. "Reporters" can use networked, portable electronic devices to provide mobile journalism content to a plurality of social media followers. Such reporters can be quickly and inexpensively deployed as the need or desire arises.

Several live-streaming social media apps and platforms can be used for transmitting video. One such video social media app is Meerkat™ that can link with a user's Twitter™ account. Meerkat™ enables a user to stream video using a handheld, networked, electronic device coupled to video capabilities. Viewers of the live-stream can comment on the stream using tweets that can be seen by and responded to by the broadcaster. Another popular app is Periscope™ that can transmit a live recording from one user to that user's Periscope™ or other social media followers. The Periscope™ app can be executed on a mobile device. The user's followers can receive an alert whenever that user begins a video transmission. Another live-stream video platform is Twitch which can be used for video streaming of video gaming, and broadcasts of various competitions, concerts and other events.

The example 1400 shows user 1410 broadcasting a video live-stream to one or more people 1450, 1460, 1470, and so on. A portable, network-enabled electronic device 1420 can be coupled to a camera 1422 that is forward facing or front facing. The portable electronic device 1420 can be a smartphone, a PDA, a tablet, a laptop computer, and so on. The camera 1422 coupled to the device 1420 can be a line-of-sight view 1424 to the user 1410 and can capture video of the user 1410. The captured video can be sent to a recommendation engine 1440 using a network link 1426 to the Internet 1430. The network link can be a wireless link, a wired link, and so on. The recommendation engine 1440 can recommend to the user 1410 an app and/or platform that can be supported by the server and can be used to provide a video live-stream to one or more followers of the user 1410. The example 1400 shows three followers 1450, 1460, and 1470 of user 1410. Each follower has a line-of-sight view to a video screen on a portable, networked electronic device. In other embodiments, one or more followers can be following the user 1410 using any other networked electronic device including a computer. In example 1400, person 1450 has line-of-sight view 1452 to the video screen of device 1454, person 1460 has line-of-sight view 1462 to the video screen of device 1464, and user 1470 has line-of-sight view 1472 to the video screen of device 1474. The portable electronic device 1454, 1564, and 1474 each can be a smartphone, a PDA, a tablet, and so on. Each portable device can receive the video stream being broadcast by user 1410 through the Internet 1430 using the app and/or platform that can be recommended by the recommendation engine 1440. Device 1454 can receive a video stream using network link 1456, device 1464 can receive a video stream using network link 1466, device 1474 can receive a video stream using network link 1476, and so on. The network link can be a wireless link, and wired link, and so on. Depending on the app and/or platform that can be recommended by the recommendation engine 1440, one or more followers, for example, followers 1450, 1460, 1470, and so on, can reply to, comment on, and otherwise provide feedback to user 1410 using their devices 1454, 1464, and 1474 respectively.

As described above, one or more videos of various types including live-streamed videos can be presented to a plurality of users for wide ranging purposes. These purposes can include, but are not limited to, entertainment, education, general information, political campaign messages, social media sharing, and so on. Mental state data can be collected from the one or users as they view the videos. The collection of the mental state data can be based on a user agreeing to enable a camera that can be used for the collection of the mental state data. The collected mental state data can be analyzed for various purposes. When the mental state data has been collected from a sufficient number of users to enable anonymity, then the aggregated mental state data can be used to provide information on aggregated mental states of the viewers. The aggregated mental states can be used to recommend videos that can include media presentations, and so on. The recommendations of videos can be based on videos that can be similar to those videos to which a user had a particular mental state response, for example. The recommendations of videos can include videos to which the user can be more likely to have a favorable mental state response, videos that can be enjoyed by the user's social media contacts, videos that can be trending, and so on.

The aggregated mental state data can be represented using a variety of techniques and can be presented to the one or more users. The aggregated mental state data can be presented while the one or more users can be viewing the video, and the aggregated mental state data can be presented after the one or more users can be viewing the video. The video can be obtained from a server, a collection of videos, a live-stream video, and so on. The aggregated mental state data can be presented to the users using a variety of techniques. For example, the aggregated mental state data can be displayed as colored dots, as graphs, etc. The colored dots, graphs, and so on, can be displayed with the video, embedded in the video, viewed subsequently to viewing the video, or otherwise presented. The aggregated mental state data can also be used to provide feedback to the originator of the video, where the feedback can include viewer reaction or reactions to the video, receptiveness to the video, effectiveness of the video, etc. The aggregated mental state data can include one of a group consisting of sadness, happiness, frustration, confusion, disappointment, hesitation, cognitive overload, focusing, being engaged, attending, boredom, exploration, confidence, trust, delight, valence, skepticism, satisfaction, and so on. The videos can include live-streamed videos. The videos and the live-streamed videos can be presented along with the aggregated mental state data from the one or more users. The aggregated mental state data as viewed by the users can be used by the users to determine what mental states can be experienced by the other users as the users view a given video, when those mental states occur, whether those mental states are similar to the one or more mental states experienced by the user, and so on. The viewing of the aggregated mental state data can enable a viewer to experience videos viewed by others, to feel connected to other users who are viewing the videos, to share in the experience of viewing the videos, to gauge the mental states experienced by the users, and so on.

The collecting of mental state data can be performed as one or more users observe the videos described above. For example, a news site, a social media site, a crowd-sourced site, an individual's digital electronic device, and so on can provide the videos. The mental state data can be collected as the one or more users view a given video or live-stream video. The mental state data can be recorded and analyzed. The results of the analysis of the collected mental state data from the one or more users can be displayed to the one or more users following the viewing of the video, for example. For confidentiality reasons, mental state data can be collected from a minimum or threshold number of users before the aggregated mental state data is displayed. One or more users on one or more social media sites can share their individual mental state data and the aggregated mental state data that can be collected. For example, a user could share with their Facebook™ friends her or his mental state data results from viewing a particular video. How a user responds to a video can be compared to the responses of their friends, of other users, and so on using a variety of techniques including a social graph. For example, the user could track the reactions of her or his friends to a particular video using a Facebook™ social graph. The mental state data can be shared automatically or can be shared manually, as selected by the user. Automatic sharing of mental state data can be based on user credentials such as logging in to a social media site. A user's privacy can also be enabled using a variety of techniques including anonymizing a user's mental state data, anonymizing and/or deleting a user's facial data, and so on. Facial tracking data can be provided in real time. In embodiments, the user can have full control of playback of a video, a streamed video, a live-streamed video, and so on. That is, the user can pause, skip, scrub, go back, stop, and so on. Recommendations can be made to the user regarding viewing another video. The flow of a user viewing a video can continue from the current video to another video based on the recommendations. The next video can be a streamed video, a live-streamed video, and so on.

In another embodiment, aggregated mental state data can be used to assist a user to select a video, video stream, live-stream video and so on that can be most engaging to the user. Consider a user who is interested in a particular type of video stream such as a gaming stream, a sports stream, a news stream, a movie stream, and so on, and that a favorite video stream is not currently available to the user. Recommendations can be made to the user based on a variety of criteria to assist the user to find an engaging video stream. For example, the user can connect to a video stream that is presenting one or more sports events but the stream does not include the stream of the user's favorite. Recommendations can be made to the user based on aggregated mental state data of other users who are ranking or reacting to the one or more sports events currently available. Similarly, if analysis of the mental state data collected from the user indicates that the user is not reacting favorably to a given video stream, then a recommendation can be made for another video stream based on an audience who is engaged with the latter stream.

A given user can choose to participate in collection of mental state data for a variety of purposes. One or more personae can be used to characterize or classify a given user who views one or more videos. The personae can be useful for recommending one or more videos to a user based on mental state data collected from the user, for example. The recommending of one or more videos to the user can be based on aggregated mental state data collected from one or more users with a similar persona. Many personae can be described and chosen based on a variety of criteria. For example, personae can include a demo user, a social sharer, a video viewing enthusiast, a viral video enthusiast, an analytics research, a quantified self-user, a music aficionado, and so on. Any number of personae can be described, and any number of personae can be assigned to a particular user.

A demo user can be a user who is curious about the collection of mental state data and the presentation of that mental state data. The demo user can view any number of videos in order to experience the mental state data collection and to observe their own social curve, for example. The demo user can view some viral videos in order to observe an aggregated population. The demo user can be interested in trying mental state data collection and presentation in order to determine how she or he would use such a technique for their own purposes.

A social sharer can be a user who is enthusiastic about sharing demos and videos with their friends. The friends can be social media friends such as Facebook™ friends, for example. The videos can be particularly engaging, flashy, slickly produced, and so on. The social sharer can be interested in the reactions to and the sharing of the video that the social sharer has shared. The social sharer can also compare their own mental states to those of their friends. The social sharer can use the comparison to increase their knowledge of their friends and to gather information about the videos that those friends enjoyed.

A video-viewing enthusiast can be a user who enjoys watching videos and once she or he has begun watching videos desires to watch more videos. Such a persona can generally stay within the context of a video streaming site, for example. The viewing by the user may be influenced by recommendations that can draw the user back to view more videos. When the user finds that the recommendations are desirable then the user likely can continue watching videos within the streaming site. The video enthusiast can want to find the videos that the user wants to watch and the portions of the videos that the user wants to watch.

A viral video enthusiast can be a user who chooses to watch many videos through social media. The social media can include links, shares, comments, etc. from friends of the user, for example. When the user clicks on the link to the video, the user can be connected from the external site to the video site. For example, the user can click a link in Reddit™ Twitter™, Facebook™, etc. and be connected to a video on YouTube™ or other video sharing site. Such a user is interested in seamless integration between the link on the social media site and the playing of the video on the video streaming site. The video streaming site can be a live-streaming video site.

An analytics researcher or "uploader" can be a user who can be interested in tracking video performance of one or more videos over time. The performance of the one or more videos can be based on various metrics including emotional engagement of one or more viewers as they view the one or more videos. The analytics researcher can be interested primarily in the various metrics that can be generated based on a given video. The analytics can be based on demographic data, geographic data, and so on. Analytics can also be based on trending search terms, popular search terms, and so on, where the search terms can be identified using web facilities such as Google Trends™.

A quantified self user can be a user who can be interested studying and/or documenting her or his own video watching experiences. The qualified self user reviews her or his mental state data over time, can sort a list of viewed videos over a time period, and so on. The qualified self user can compare their mental state data collected while watching a given video with their personal norms. This user persona can also provide feedback. The quantified self user can track their reactions to one or more videos over time and over videos, where tracking over videos can include tracking favorite videos, categorizing videos that have been viewed, remembering favorite videos, etc.

A music enthusiast can be a user who can be a consumer of music who uses a video streaming site as a music streaming site. For example, this user persona can use music mixes from sites such as YouTube™ as if they were provide by a music streaming site such as Spotify™, Pandora™, Rdio™, Apple Music™, Tidal™, and so on. The music enthusiast persona can be less likely to be sitting in front of a screen since their main mode of engagement is sound rather than sight. Facial reactions that can be captured of the listener can be weaker, for example, than those facial reactions captured from a viewer.

The method can include comparing the mental state data that was captured against mental state event temporal signatures. In embodiments, the method can include identifying a mental state event type based on the comparing. And the recommending of the second media presentation can be based on the mental state event type. The first media presentation can include a first socially shared livestream video. The method can further comprise generating highlights for the first socially shared livestream video, based on the mental state data that was captured. The first socially shared livestream video can include an overlay with information on the mental state data that was captured. The overlay can include information on the mental state data collected from the other people. The mental state data that was captured for the first socially shared livestream video can be analyzed substantially in real time. In some embodiments, the second media presentation includes a second socially shared livestream video. The method can further comprise a recommendation for changing from the first socially shared livestream video to the second socially shared livestream video. The first socially shared livestream video can be broadcast to a plurality of people. In embodiments, the method can further comprise providing an indication to the individual that the second socially shared livestream video is ready to be joined.

Figure 15:
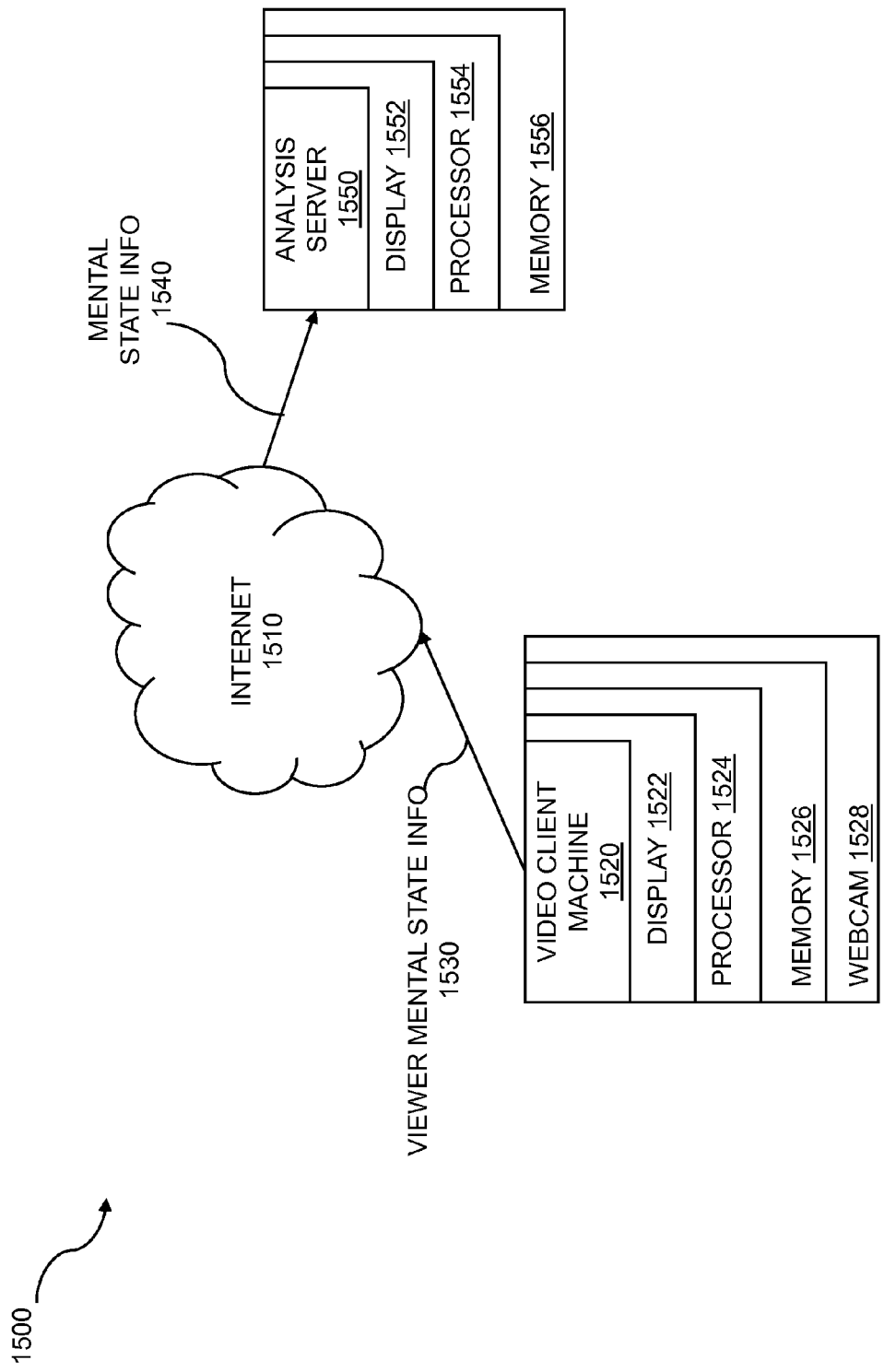
FIG. 15 is a system diagram for analyzing mental state information.

FIG. 15 is a system diagram for analyzing mental state information. The system 1500 may include the Internet 1510, intranet, or other computer network, which may be used for communication between or among the various computers of the system 1500. A video client machine or client computer 1520 has a memory 1526 which stores instructions, and one or more processors 1524 attached to the memory 1526 wherein the one or more processors 1524 can execute instructions stored in the memory 1526. The memory 1526 may be used for storing instructions, for storing mental state data, for system support, and the like. The client computer 1520 also may have an Internet connection to carry viewer mental state information 1530, and a display 1522 that may present various videos to one or more viewers. The client computer 1520 may be able to collect mental state data from one or more viewers as they observe the video or videos. In some embodiments there may be multiple client computers 1520 that collect mental state data from viewers as they observe a video. The video client computer 1520 may have a camera, such as a webcam 1528, for capturing viewer interaction with a video including, in some embodiments, video of the viewer. The camera 1528 may refer to a webcam, a camera on a computer (such as a laptop, a net-book, a tablet, or the like), a video camera, a still camera, a cell phone camera, a mobile device camera (including, but not limited to, a forward facing camera), a thermal imager, a CCD device, a three-dimensional camera, a depth camera, and multiple webcams used to capture different views of viewers or any other type of image capture apparatus that may allow image data captured to be used by the electronic system.

Once the mental state data has been collected, the client computer may upload information to a server or analysis computer 1550, based on the mental state data from the plurality of viewers who observe the video. The client computer 1520 may communicate with the server 1550 over the Internet 1510, intranet, some other computer network, or by any other method suitable for communication between two computers. In some embodiments, the analysis computer 1550 functionality may be embodied in the client computer.

The analysis computer 1550 may have a connection to the Internet 1510 to enable mental state information 1540 to be received by the analysis computer 1550. Further, the analysis computer 1550 may have a memory 1556 which stores instructions, data, help information and the like, and one or more processors 1554 attached to the memory 1556 wherein the one or more processors 1554 can execute instructions. The memory 1556 may be used for storing instructions, for storing mental state data, for system support, and the like. The analysis computer 1550 may use the Internet 1510, or other computer communication method, to obtain mental state information 1540. The analysis computer 1550 may receive mental state information collected from a plurality of viewers from the client computer or computers 1520, and may aggregate mental state information on the plurality of viewers who observe the video.

The analysis computer 1550 may process mental state data or aggregated mental state data gathered from a viewer or a plurality of viewers to produce mental state information about the viewer or plurality of viewers. In some embodiments, the analysis server 1550 may obtain mental state information 1530 from the video client 1520. In this case the mental state data captured by the video client 1520 was analyzed by the video client 1520 to produce mental state information for uploading. Based on the mental state information produced, the analysis server 1550 may project a value based on the mental state information for one or more videos. The analysis computer 1550 may also associate the aggregated mental state information with the rendering and also with the collection of norms for the context being measured.

In some embodiments, the analysis computer 1550 may receive or provide aggregated mental state information based on the mental state data from the plurality of viewers who observe the video and may present aggregated mental state information in a rendering on a display 1552. In some embodiments, the analysis computer may be set up for receiving mental state data collected from a plurality of viewers as they observe the video, in a real-time or near real-time embodiment. In at least one embodiment, a single computer may incorporate the client, server and analysis functionalities. Viewer mental state data may be collected from the client computer or computers 1520 to form mental state information on the viewer or plurality of viewers viewing a video. The mental state information resulting from the analysis of the mental state date of a viewer or a plurality of viewers may be used to project a video value based on the mental state information. The system 1500 may include computer program product embodied in a non-transitory computer readable medium comprising: code for playing a first media presentation to an individual, code for capturing mental state data for the individual while the first media presentation is played, and code for recommending a second media presentation to the individual based on the mental state data for the individual which was captured. The system 1500 may include capabilities for affect-based recommendation comprising: a memory for storing instructions, one or more processors attached to the memory wherein the one or more processors are configured to play a first media presentation to an individual, capture mental state data for the individual while the first media presentation is played, and recommend a second media presentation to the individual based on the mental state data for the individual which was captured. The system 1500 may include computer program product embodied in a non-transitory computer readable medium comprising: code for selecting a video; code for embedding the video within a web-enabled interface wherein the web-enabled interface activates collecting of mental state data; and code for distributing the web-enabled interface. The system 1500 may include capabilities for rendering video comprising: a memory for storing instructions; one or more processors attached to the memory wherein the one or more processors are configured to: select a video; embed the video within a web-enabled interface wherein the web-enabled interface activates collecting of mental state data; and distribute the web-enabled interface.

The above methods may be executed on one or more processors on one or more computer systems. Embodiments may include various forms of distributed computing, client/server computing, and cloud based computing. Further, it will be understood that for the flow diagrams in this disclosure, the depicted steps or boxes are provided for purposes of illustration and explanation only. The steps may be modified, omitted, or re-ordered and other steps may be added without departing from the scope of this disclosure. Further, each step may contain one or more sub-steps. While the foregoing drawings and description set forth functional aspects of the disclosed systems, no particular arrangement of software and/or hardware for implementing these functional aspects should be inferred from these descriptions unless explicitly stated or otherwise clear from the context. All such arrangements of software and/or hardware are intended to fall within the scope of this disclosure.

The block diagrams and flow diagram illustrations depict methods, apparatus, systems, and computer program products. Each element of the block diagrams and flow diagram illustrations, as well as each respective combination of elements in the block diagrams and flow diagram illustrations, illustrates a function, step or group of steps of the methods, apparatus, systems, computer program products and/or computer-implemented methods. Any and all such functions may be implemented by computer program instructions, by special-purpose hardware-based computer systems, by combinations of special purpose hardware and computer instructions, by combinations of general purpose hardware and computer instructions, by a computer system, and so on. Any and all of which may be generally referred to herein as a "circuit," "module," or "system."

A programmable apparatus which executes any of the above mentioned computer program products or computer implemented methods may include one or more processors, microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are not limited to applications involving conventional computer programs or programmable apparatus that run them. It is contemplated, for example, that embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized. The computer readable medium may be a non-transitory computer readable medium for storage. A computer readable storage medium may be electronic, magnetic, optical, electromagnetic, infrared, semiconductor, or any suitable combination of the foregoing. Further computer readable storage medium examples may include an electrical connection having one or more wires, a portable computer diskette, a hard disk, a random access memory (RAM), a read-only memory (ROM), an erasable programmable read-only memory (EPROM), Flash, MRAM, FeRAM, phase change memory, an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed more or less simultaneously to enhance utilization of the processor and to facilitate substantially simultaneous functions. By way of implementation, any and all methods, program codes, program instructions, and the like described herein may be implemented in one or more thread. Each thread may spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the entity causing the step to be performed.

While the invention has been disclosed in connection with preferred embodiments shown and described in detail, various modifications and improvements thereon will become apparent to those skilled in the art. Accordingly, the spirit and scope of the present invention is not to be limited by the foregoing examples, but is to be understood in the broadest sense allowable by law.

What is claimed is:

1. A computer-implemented method for affect based recommendations comprising:
    playing a first media presentation to an individual;
    capturing mental state data, wherein the mental state data includes facial data, for the individual, while the first media presentation is played;
    comparing the mental state data that was captured against mental state event temporal signatures;
    inferring mental states, using one or more processors, based on the mental state data which was collected and analysis of the facial data for at least brow furrows;
    correlating the mental state data which was captured for the individual to mental state data collected from other people who experienced the first media presentation, wherein the correlating is based on identifying and using maximally dissimilar responses during part of the correlating;
    ranking the first media presentation relative to another media presentation based on the mental state data which was captured, wherein the ranking is for the individual based on the mental state data captured from the individual; and
    recommending a second media presentation to the individual based on the mental state data for the individual which was captured wherein the recommending the second media presentation to the individual is further based on the correlating between the individual and the other people.

2. The method of claim 1 further comprising identifying a mental state event type based on the comparing.

3. The method of claim 2 wherein the recommending of the second media presentation is further based on the mental state event type.

4. The method of claim 1 wherein the first media presentation includes a first socially shared livestream video.

5. The method of claim 4 further comprising generating highlights for the first socially shared livestream video, based on the mental state data that was captured.

6. The method of claim 4 wherein the first socially shared livestream video includes an overlay with information on the mental state data that was captured.

7. The method of claim 6 wherein the overlay includes information on the mental state data collected from the other people.

8. The method of claim 4 wherein the mental state data that was captured for the first socially shared livestream video is analyzed substantially in real time.

9. The method of claim 4 wherein the second media presentation includes a second socially shared livestream video.

10. The method of claim 9 further comprising a recommendation for changing from the first socially shared livestream video to the second socially shared livestream video.

11. The method of claim 9 wherein the first socially shared livestream video is broadcast to a plurality of people.

12. The method of claim 11 further comprising providing an indication to the individual that the second socially shared livestream video is ready to be joined.

13. The method of claim 1 further comprising analyzing the mental state data to produce mental state information.

14. The method according to claim 1 wherein the first media presentation includes one of a group consisting of a movie, a television show, a web series, a webisode, a video, a video clip, an electronic game, an e-book, and an e-magazine.

15. The method according to claim 1 wherein the second media presentation includes one of a group consisting of a movie, a television show, a web series, a webisode, a video, a video clip, an electronic game, an e-book, and an e-magazine.

16. The method according to claim 1 wherein the first media presentation is played on a web-enabled interface.

17. A computer program product embodied in a non-transitory computer readable medium comprising:

code for playing a first media presentation to an individual;

code for capturing mental state data, wherein the mental state data includes facial data, for the individual while the first media presentation is played;

code for inferring mental states, executed on one or more processors, based on the mental state data which was collected and analysis of the facial data for at least brow furrows;

code for correlating the mental state data which was captured for the individual to mental state data collected from other people who experienced the first media presentation, wherein the correlating is based on identifying and using maximally dissimilar responses during part of the correlating;

code for ranking the first media presentation relative to another media presentation based on the mental state data which was captured; and code for recommending a second media presentation to the individual based on the mental state data for the individual which was captured wherein the recommending the second media presentation to the individual is further based on the correlating between the individual and the other people.

18. A computer system for affect based recommendations comprising:

a memory for storing instructions;

one or more processors attached to the memory wherein the one or more processors are configured to:

play a first media presentation to an individual;

capture mental state data, wherein the mental state data includes facial data, for the individual while the first media presentation is played;

infer mental states, using the one or more processors, based on the mental state data which was collected and analysis of the facial data for at least brow furrows;

correlate the mental state data which was captured for the individual to mental state data collected from other people who experienced the first media presentation, wherein the correlating is based on identifying and using maximally dissimilar responses during part of the correlating;

rank the first media presentation relative to another media presentation based on the mental state data which was captured; and recommend a second media presentation to the individual based on the mental state data for the individual which was captured wherein recommendation of the second media presentation to the individual is further based on correlation between the individual and the other people.

* * * * *